United States Patent
Netabayashi et al.

(10) Patent No.: US 12,186,121 B2
(45) Date of Patent: Jan. 7, 2025

(54) MEDICAL IMAGE DIAGNOSTIC APPARATUS, MEDICAL INFORMATION PROCESSING SYSTEM, AND COMPUTER PROGRAM PRODUCT

(71) Applicant: CANON MEDICAL SYSTEMS CORPORATION, Tochigi (JP)

(72) Inventors: Tomoyuki Netabayashi, Nasushiobara (JP); Masaki Yoshida, Yaita (JP); Kazuki Gatayama, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 583 days.

(21) Appl. No.: 17/495,953

(22) Filed: Oct. 7, 2021

(65) Prior Publication Data
US 2022/0104784 A1    Apr. 7, 2022

(30) Foreign Application Priority Data

Oct. 7, 2020  (JP) .................................. 2020-169535
Sep. 30, 2021 (JP) .................................. 2021-161445

(51) Int. Cl.
*A61B 6/00*   (2024.01)
*A61B 6/03*   (2006.01)

(52) U.S. Cl.
CPC ............ *A61B 6/5205* (2013.01); *A61B 6/032* (2013.01); *A61B 6/44* (2013.01)

(58) Field of Classification Search
CPC ........ G16H 40/63; G16H 30/20; G16H 30/40; A61B 6/54; A61B 6/5205; A61B 6/44; A61B 6/032; A61B 6/488; A61B 6/5294; A61B 6/5211; A61B 6/545; A61B 6/465; A61B 6/469; A61B 6/0407; A61B 6/461; A61B 6/563; A61B 6/566; A61B 6/4488; A61B 6/466; A61B 6/542; A61B 6/50; A61B 6/4035; A61B 6/06; A61B 6/463; A61B 6/4085; A61B 6/547; A61B 6/025; A61B 6/5223; A61B 5/742; A61B 6/037;
(Continued)

(56) References Cited

U.S. PATENT DOCUMENTS 9,734,298 B2 * 8/2017 Hall ...................... G16H 50/20
2012/0183191 A1   7/2012 Nakamura
(Continued)

FOREIGN PATENT DOCUMENTS

JP  2005-80969 A   3/2005
JP  2011-92682 A   5/2011
(Continued)

*Primary Examiner* — Irakli Kiknadze
(74) *Attorney, Agent, or Firm* — Oblon, McClelland, Maier & Neustadt, L.L.P.

(57) ABSTRACT

A medical image diagnostic apparatus of an embodiment includes processing circuitry. The processing circuitry executes a scan based on a protocol designated by a user. The processing circuitry extracts a candidate protocol to be executed next to the protocol, based on protocol order information in which identification information that indicates each of a plurality of candidate protocols that can be executed starting from a specific protocol, and order information in which each candidate protocol is executed, are correlated with each other. The processing circuitry outputs the extracted candidate protocol.

22 Claims, 26 Drawing Sheets

(58) Field of Classification Search
CPC ....... A61B 6/04; A61B 6/0487; A61B 6/4417;
A61B 6/5235; A61B 5/0044; A61B
5/0245; A61B 5/044; A61B 5/055; A61B
5/7289; A61B 5/7292; A61B 6/503; A61B
6/5288; A61B 6/541; A61B 2576/023;
A61B 6/4291; G06T 7/0012; G06T
11/008; G06T 11/006; G06T 19/00; G06T
2207/20004; G06T 2207/10081; G06T
2219/008; G06T 2211/421; G06T
2219/028; G06T 2200/04; G06T 11/60;
G06T 2200/24; G06T 2210/41; G06T
7/70; G06T 11/005; G06T 2207/20036;
G06T 2207/10104; G06T 2207/30242;
G06T 2207/20081; G06T 2207/30004;
G06T 2211/441; G06F 3/0482; G06F
3/04847; G06F 3/0486; G06F
2203/04803; G09B 23/286; G01R 33/546;
G01R 33/5673
USPC .................................................. 378/4, 19, 62
See application file for complete search history.

(56) References Cited

U.S. PATENT DOCUMENTS

| | | | |
|---|---|---|---|
| 2013/0311200 A1* | 11/2013 | Cohen-Solal | G16H 50/70 |
| | | | 705/2 |
| 2014/0180106 A1 | 6/2014 | Takahashi et al. | |
| 2015/0063535 A1 | 3/2015 | Gatayama et al. | |
| 2015/0182173 A1* | 7/2015 | Yang | G01R 33/546 |
| | | | 600/407 |
| 2017/0181722 A1 | 6/2017 | Gatayama et al. | |
| 2018/0206811 A1 | 7/2018 | Gatayama et al. | |
| 2019/0247024 A1 | 8/2019 | Takahashi et al. | |

FOREIGN PATENT DOCUMENTS

| | | |
|---|---|---|
| JP | 2011-177399 A | 9/2011 |
| JP | 2017-12592 A | 1/2017 |
| JP | 6116831 B2 | 4/2017 |
| JP | 2018-118045 A | 8/2018 |
| JP | 6605195 B2 | 11/2019 |

* cited by examiner

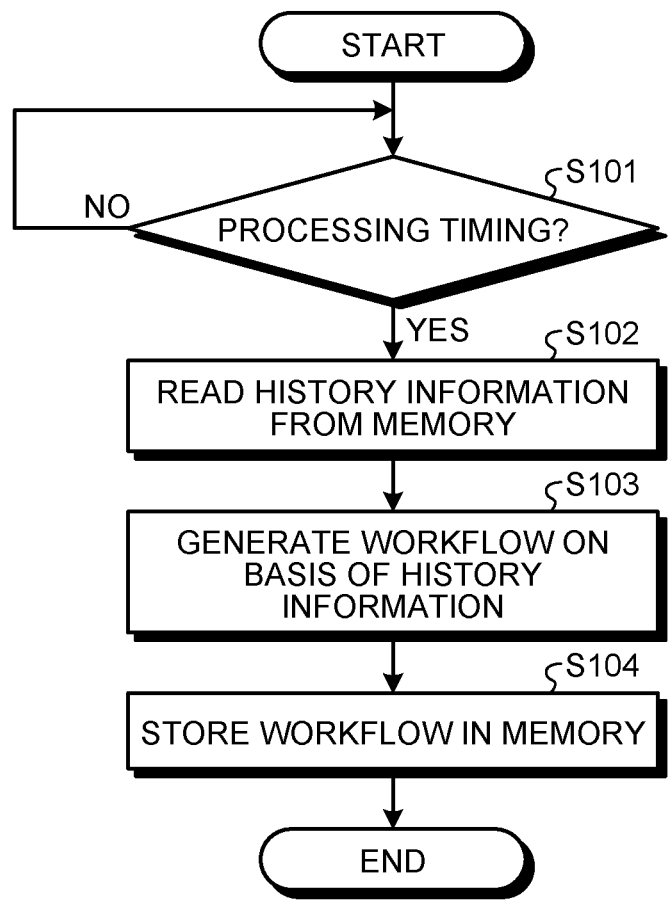

FIG.6F
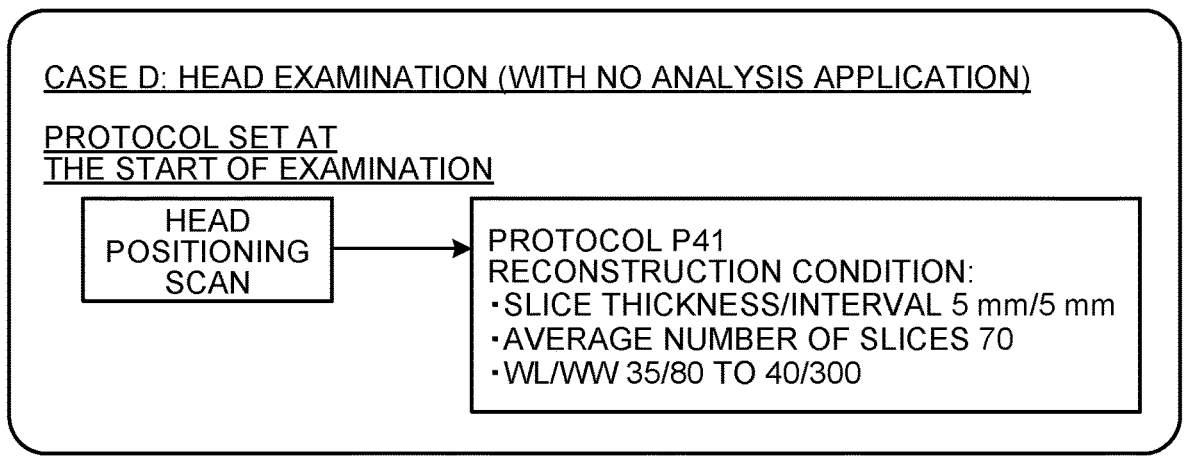
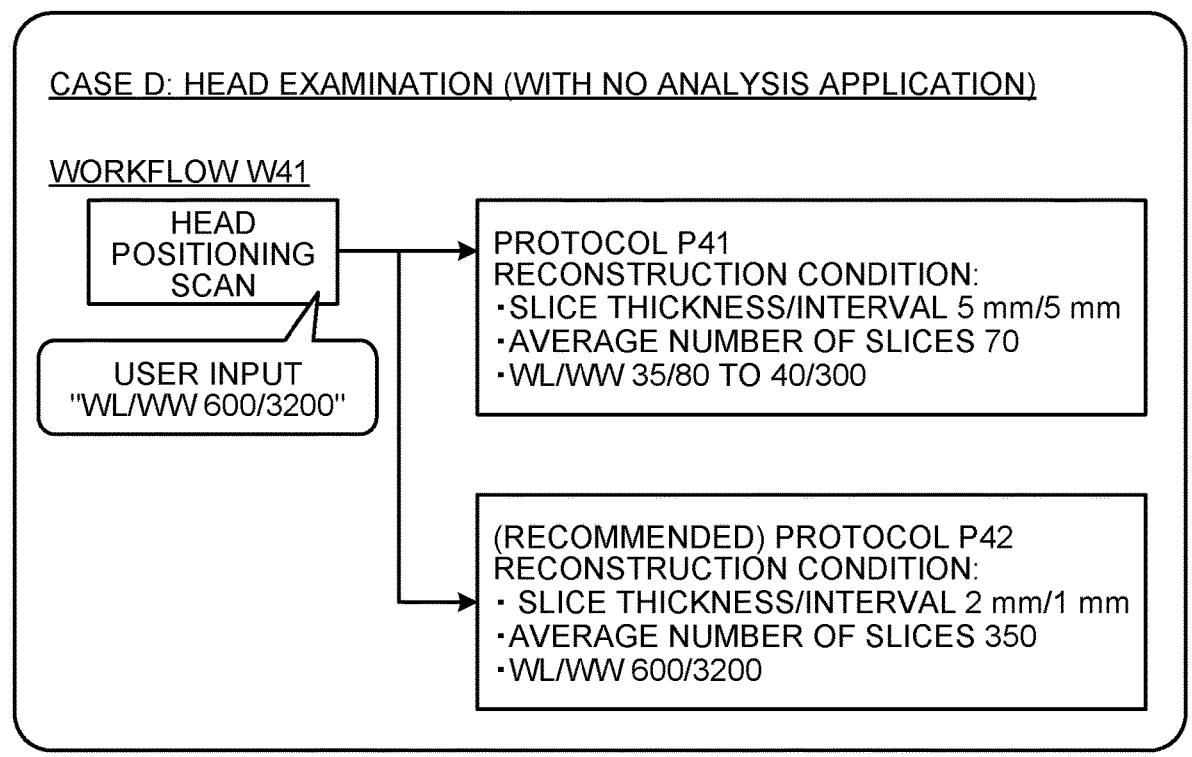

MEDICAL IMAGE DIAGNOSTIC APPARATUS, MEDICAL INFORMATION PROCESSING SYSTEM, AND COMPUTER PROGRAM PRODUCT

CROSS-REFERENCE TO RELATED APPLICATIONS

This application is based upon and claims the benefit of priority from Japanese Patent Application No. 2020-169535, filed on Oct. 7, 2020; and Japanese Patent Application No. 2021-161445, filed on Sep. 30, 2021, the entire contents of which are incorporated herein by reference.

FIELD

Embodiments described herein relate generally to a medical image diagnostic apparatus, a medical information processing system, and a computer program product.

BACKGROUND

In the related art, in imaging using an X-ray computed tomography (CT) apparatus, a scan protocol (hereinafter, also simply referred to as a "protocol") for collecting data according to an examination site and examination content is set. The protocol is set by selecting a protocol that is suitable for the examination site and the examination content from a plurality of protocols in which various conditions have been preset, and appropriately adjusting the preset conditions. Here, each protocol is classified according to, for example, age, adult/child, male/female, physiques such as weight and height, an examination purpose, and the like, and various conditions are preset, such as an imaging range of a positioning image (scanogram image) for setting the imaging range, an imaging angle of the scanogram image, a tube voltage and a tube current when imaging the positioning image, a scan method for main imaging (scan) for collecting data to be used for diagnosis, a scan position, a scan range, a tube voltage and a tube current when executing a scan, and a position and a range of image reconstruction.

In CT imaging, a scan may be executed using a specific protocol and then protocols for next imaging may be appropriately selected. For example, when a positioning scan such as "whole body scan" is executed as a first scan, a protocol for local imaging is selected as a second scan. Furthermore, when a scan called "Ca Score" for measuring an Agatston score is executed as the first scan, a protocol corresponding to the measured value (Agatston score) is selected as the second scan. In such a case, a user sequentially selects protocols for next imaging according to a result of the executed scan. Alternatively, the user generates in advance a plurality of protocols to be executed and a continuous protocol that strictly defines the order thereof, and performs imaging by using the continuous protocol.

BRIEF DESCRIPTION OF THE DRAWINGS

FIG. 2 is a flowchart illustrating a processing procedure of a generation process by the X-ray CT apparatus according to the first embodiment;

FIG. 6A to 6F are diagrams for explaining the extraction process of an extraction function according to the first embodiment;

DETAILED DESCRIPTION

A medical image diagnostic apparatus of an embodiment includes processing circuitry. The processing circuitry executes a scan on the basis of a protocol designated by a user. The processing circuitry extracts a candidate protocol to be executed next to the protocol, on the basis of protocol order information in which identification information which indicates each of a plurality of candidate protocols that can be executed starting from a specific protocol, and order information in which each candidate protocol is executed, are correlated with each other. The processing circuitry outputs the extracted candidate protocol.

Hereinafter, a medical image diagnostic apparatus, a medical information processing system, and a computer program product according to embodiments will be described with reference to the drawings. Note that embodiments are not limited to the following embodiments. Furthermore, content described in one embodiment can also be similarly applied to other embodiments in principle.

First Embodiment

Figure 1:
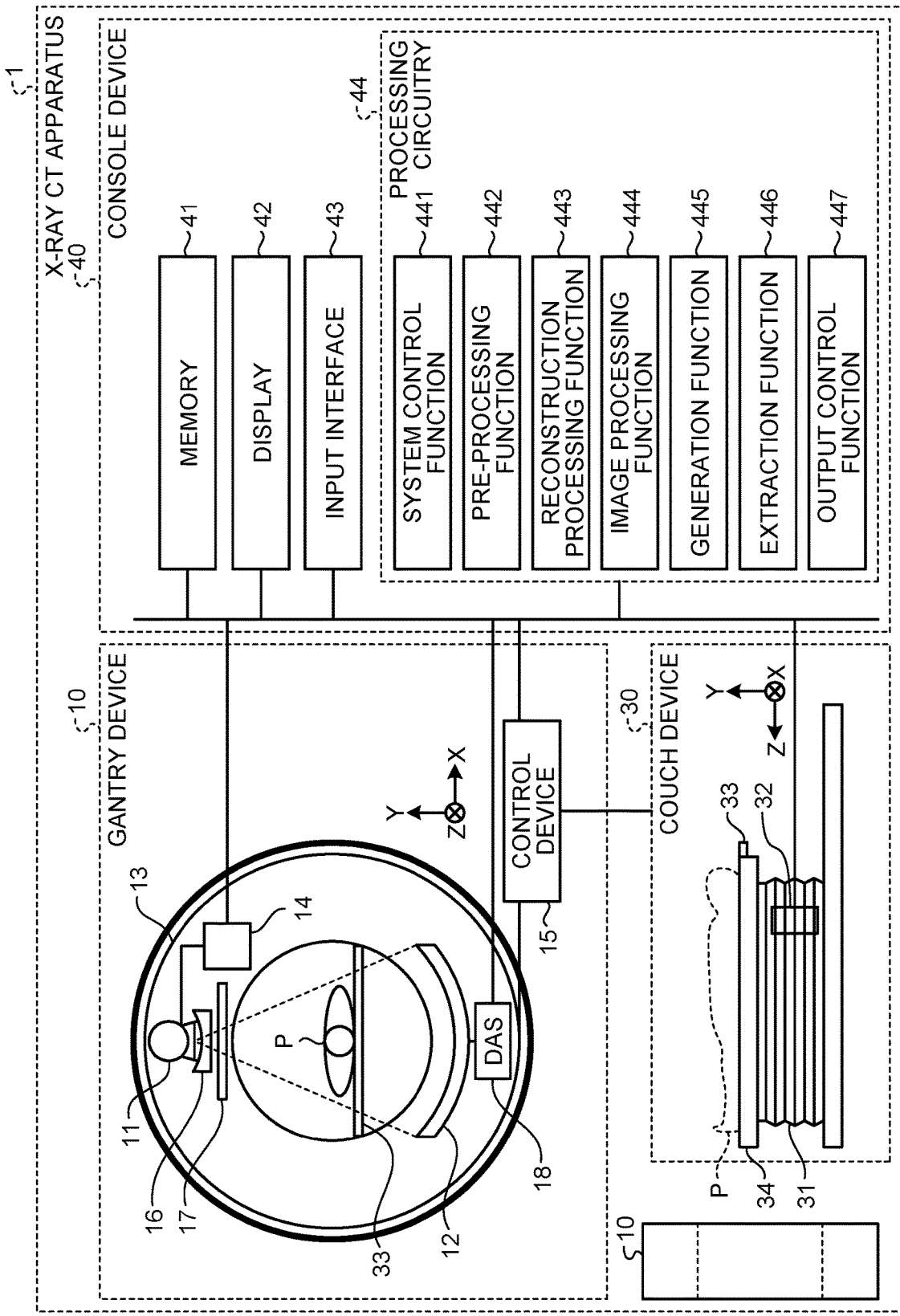
FIG. 1 is a block diagram illustrating an example of a configuration of an X-ray CT apparatus according to a first embodiment.

FIG. 1 is a block diagram illustrating an example of a configuration of an X-ray CT apparatus according to a first embodiment. As illustrated in FIG. 1, an X-ray CT apparatus 1 according to the first embodiment has a gantry device 10, a couch device 30, and a console device 40. Note that in FIG. 1, the gantry device 10 are drawn at two locations for convenience of illustration, but typically, one X-ray CT apparatus 1 includes one gantry device 10.

Note that in the present embodiment, the longitudinal direction of a rotating shaft of a rotating frame 13 or a couchtop 33 of the couch device 30 in a non-tilted state is defined as a Z-axis direction. Furthermore, an axial direction orthogonal to the Z-axis direction and horizontal to a floor surface is defined as an X-axis direction. Furthermore, an axial direction orthogonal to the Z-axis direction and perpendicular to the floor surface is defined as a Y-axis direction.

The gantry device 10 has an X-ray tube 11, an X-ray detector 12, the rotating frame 13, an X-ray high voltage device 14, a control device 15, a wedge 16, a collimator 17, and a data acquisition system (DAS) 18.

The X-ray tube 11 is a vacuum tube that generates X-rays by emitting thermoelectrons toward an anode (target) from a cathode (filament) by the application of a high voltage from the X-ray high voltage device 14. For example, an example of the X-ray tube 11 includes a rotating anode type X-ray tube that generates X-rays by emitting thermoelectrons to a rotating anode.

The wedge 16 is a filter for adjusting the dose of the X-rays emitted from the X-ray tube 11. Specifically, the wedge 16 is a filter that attenuates the X-rays emitted from the X-ray tube 11 by allowing the X-rays to pass therethrough so that the X-rays emitted from the X-ray tube 11 to a subject P have a predetermined distribution. For example, the wedge 16 is a filter made of aluminum so as to have a predetermined target angle and a predetermined thickness. The wedge 16 may be called a wedge filter or a bow-tie filter.

The collimator 17 is a lead plate and the like for narrowing down the emission range of the X-rays having passed through the wedge 16 and forms a slit by a combination of a plurality of lead plates and the like. Note that the collimator 17 is also referred to as an X-ray diaphragm.

The X-ray detector 12 detects the X-rays emitted from the X-ray tube 11 and passed through the subject P, and outputs an electric signal corresponding to the dose of the X-rays to the DAS 18. The X-ray detector 12 has, for example, a plurality of X-ray detection element arrays in which a plurality of X-ray detection elements are arranged in a channel direction along one arc centered on a focal point of the X-ray tube. The X-ray detector 12 has, for example, a structure in which the X-ray detection element arrays with the X-ray detection elements arranged in the channel direction are arranged in a slice direction (column direction and row direction).

Furthermore, the X-ray detector 12 is an indirect conversion type detector having, for example, a grid, a scintillator array, and an optical sensor array. The scintillator array has a plurality of scintillators, and each of the scintillators has a scintillator crystal that outputs light with a photon quantity corresponding to an incident X-ray dose. The grid has an X-ray shielding plate that is disposed on the surface of the scintillator array on an X-ray incident side and has a function of absorbing scattered X-rays. Note that the grid is also be referred to as a collimator (one-dimensional collimator or two-dimensional collimator). The optical sensor array has a function of converting light into an electric signal corresponding to the amount of light from the scintillator, and has, for example, an optical sensor such as a photomultiplier (PMT). Note that the X-ray detector 12 may be a direct conversion type detector having a semiconductor element that converts the incident X-rays into an electric signal. Furthermore, the X-ray detector 12 is an example of an X-ray detector.

The X-ray high voltage device 14 has an electric circuitry such as a transformer and a rectifier, and has a high voltage generation device having a function of generating a high voltage to be applied to the X-ray tube 11 and an X-ray control device that controls an output voltage corresponding to the X-rays emitted by the X-ray tube 11. The high voltage generation device may be of a transformer type or an inverter type. Note that the X-ray high voltage device 14 may be provided on the rotating frame 13 to be described below, or may also be provided on a fixed frame (not illustrated) side of the gantry device 10. Note that the fixed frame is a frame that rotatably supports the rotating frame 13. Note that the X-ray high voltage device 14 is an example of an X-ray high voltage unit.

The DAS 18 has an amplifier that performs an amplification process on the electric signals output from each X-ray detector element of the X-ray detector 12 and an A/D converter that converts the electric signal to a digital signal, and generates detection data. The detection data generated by the DAS 18 is transferred to the console device 40. Furthermore, the DAS 18 is an example of a data collection unit.

The rotating frame 13 is an annular frame that supports the X-ray tube 11 and the X-ray detector 12 so as to face each other and rotates the X-ray tube 11 and the X-ray detector 12 by the control device 15 to be described below. Note that the rotating frame 13 further includes the X-ray high voltage device 14 and the DAS 18 in addition to the X-ray tube 11 and the X-ray detector 12, and supports the X-ray high voltage device 14 and the DAS 18. Note that the detection data generated by the DAS 18 is transmitted by optical communication from a transmitter having a light emitting diode (LED) provided in the rotating frame to a receiver provided in a non-rotating part (for example, a fixed frame and not illustrated in FIG. 1) of the gantry device and having a photodiode, and is transferred to the console device 40. Note that the transmission method of the detection data from the rotating frame to the non-rotating part of the gantry device is not limited to the aforementioned optical communication, and may adopt any method as long as it is a non-contact type data transmission. Furthermore, the rotating frame 13 is an example of a rotating unit.

The control device 15 has processing circuitry having a CPU and the like, and a driving mechanism such as a motor and an actuator. The control device 15 has a function of receiving an input signal from an input interface 43 to be described below, which is attached to the console device 40 or the gantry device 10, and controlling the operations of the gantry device 10 and the couch device 30. For example, the control device 15 receives the input signal and performs control of rotating the rotating frame 13, tilting the gantry device 10, and operating the couch device 30 and the couchtop 33. Note that the control of tilting the gantry device 10 is implemented by the control device 15 that rotates the rotating frame 13 around an axis parallel to the X-axis direction based on information on inclination angle (tilt angle) information input by the input interface attached to the gantry device 10. Note that the control device 15 may be provided in the gantry device 10 or may also be provided in the console device 40.

The couch device 30 is a device that places and moves the subject P to be scanned and includes a pedestal 31, a couch driving device 32, the couchtop 33, and a support frame 34. The pedestal 31 is a casing that supports the support frame 34 so as to be movable in a vertical direction. The couch driving device 32 includes processing circuitry having a CPU and the like and a driving mechanism such as a motor and an actuator, and controls the movement of the couchtop 33 and the support frame 34. The couchtop 33 is a plate on which the subject P is placed and is provided on an upper surface of the support frame 34. The support frame 34 is a member that supports the couchtop 33 so as to be movable in the long axis direction of the couchtop 33, and moves up and down together with the couchtop 33 by the operation of the pedestal 31.

The console device 40 has a memory 41, a display 42, the input interface 43, and processing circuitry 44. Although the console device 40 is described as a separate body from the gantry device 10, the gantry device 10 may include the console device 40 or some of the respective components of the console device 40.

The memory 41 is implemented by, for example, a semiconductor memory element such as a random access memory (RAM) and a flash memory, a hard disk, an optical disk, and the like. The memory 41 stores, for example, projection data and reconstructed image data. Furthermore, the memory 41 is an example of storage circuitry.

The display 42 displays various information. For example, the display 42 outputs a medical image (CT image) generated by the processing circuitry 44, a graphical user interface (GUI) for receiving various operations from an operator, and the like. For example, the display 42 is a liquid crystal display or a cathode ray tube (CRT) display. Furthermore, the display 42 may be provided on the gantry device 10. Furthermore, the display 42 may be of a desktop type, or may be composed of a tablet terminal and the like capable of wirelessly communicating with a body of the console device 40. Furthermore, the display 42 is an example of a display unit.

The input interface 43 receives various input operations from the operator, converts the received input operations into electric signals, and outputs the electric signals to the processing circuitry 44. For example, the input interface 43 receives, from the operator, collection conditions when collecting the projection data, reconstruction conditions when reconstructing the CT image, image processing conditions when generating a post-processing image from the CT image, and the like. For example, the input interface 43 is implemented by a mouse, a keyboard, a trackball, a switch, a button, a joystick, and the like. Furthermore, the input interface 43 may be provided on the gantry device 10. Furthermore, the input interface 43 may be composed of a tablet terminal and the like capable of wirelessly communicating with the body of the console device 40. Furthermore, the input interface 43 is an example of an input unit.

The processing circuitry 44 controls the overall operation of the X-ray CT apparatus 1. For example, the processing circuitry 44 performs a system control function 441, a pre-processing function 442, a reconstruction processing function 443, an image processing function 444, a generation function 445, an extraction function 446, and an output control function 447. Furthermore, the processing circuitry 44 is an example of a processing unit.

The system control function 441 controls various functions of the processing circuitry 44 on the basis of the input operations received from the operator via the input interface 43. For example, the system control function 441 controls a data collection process in the gantry device 10 by controlling the operation of the gantry device 10. Furthermore, the system control function 441 controls the operation of the gantry device 10 so that the data collection process is performed under imaging conditions designated by the operator. Furthermore, the system control function 441 is an example of a scan execution unit that executes a scan on the basis of a protocol designated by a user.

The pre-processing function 442 generates data obtained by performing pre-processing, such as logarithmic transformation processing, offset correction processing, inter-channel sensitivity correction processing, and beam hardening correction, on the detection data output from the DAS 18. Note that data (detection data) before the pre-processing and data after the pre-processing may be collectively referred to as projection data. Furthermore, the pre-processing function 442 is an example of a pre-processing unit.

The reconstruction processing function 443 generates CT image data by performing reconstruction processing using a filtered back projection method, a successive approximation reconstruction method, and the like on projection data generated by the pre-processing function 442. Furthermore, the reconstruction processing function 443 is an example of a reconstruction unit.

The image processing function 444 converts the CT image data generated by the reconstruction processing function 443 into tomographic image data or three-dimensional image data having an arbitrary section by a known method on the basis of the input operation received from the operator via the input interface 43. Note that the reconstruction processing function 443 may directly generate the three-dimensional image data. Furthermore, the image processing function 444 is an example of an image processing unit.

The generation function 445, the extraction function 446, and the output control function 447 will be described below.

Here, in the CT imaging, a scan may be executed using a specific protocol, and then protocols for next imaging may be appropriately selected. For example, when a positioning scan such as "whole body scan" is executed as a first scan, a protocol for local imaging is selected as a second scan. Furthermore, when a scan called "Ca Score" for measuring an Agatston score is executed as the first scan, a protocol corresponding to the measured value (Agatston score) is selected as the second scan. In such a case, a user sequentially selects protocols for next imaging according to a result of the executed scan (first method). Alternatively, the user generates in advance a plurality of protocols to be executed and a composite protocol that strictly defines the order thereof, and performs imaging by using the composite protocol (second method).

Note that the composite protocol is information in which the protocols to be executed are arranged in order including various information (imaging conditions, reconstruction conditions, various parameters, and the like) included in the respective protocols. Therefore, the composite protocol strictly defines a protocol to be executed next to a certain protocol and does not include protocol options. Furthermore, since the composite protocol is integrated as "one protocol" including information included in all the protocols to be executed in order, various information included in the respective are all registered.

However, when the protocols for next imaging are sequentially selected (first method), the protocols for next imaging are selected from many options stored in the X-ray CT apparatus 1 according to a result of a previous scan. Therefore, inexperienced users (medical workers such as doctors and engineers) or users having a different field of specialization may take extra time to select an appropriate protocol.

Furthermore, when the composite protocol is used (second method), the work of selecting a protocol does not occur, but composite protocols corresponding to all options are individually generated, resulting in a significant increase in the number of protocols to be managed. Furthermore, when conditions of a scan that tends to be included in many composite protocols, such as a positioning scan, are partially changed, it is necessary to change a plurality of composite protocols including the conditions, resulting in a significant increase in the management load.

In this regard, the X-ray CT apparatus 1 according to the first embodiment performs the following processing in order to easily select an appropriate protocol. That is, the X-ray CT apparatus 1 executes a scan on the basis of a protocol designated by a user. Then, the X-ray CT apparatus 1 extracts a candidate protocol to be executed next to the protocol of the executed scan, on the basis of a workflow, in which identification information indicating each of a plurality of candidate protocols that can be executed starting from a specific protocol and selection conditions for selecting each candidate protocol are correlated with each other, and the result of the scan. Then, the X-ray CT apparatus 1 outputs the extracted candidate protocol.

Note that the workflow used in the present embodiment is information indicating options (choices) of a protocol that can be executed next to a specific protocol. Furthermore, since the workflow is information indicating the order and options of each protocol by the identification information of each protocol, the workflow does not basically include various information included in each protocol. Note that the workflow is an example of "branch information (protocol branch information)" indicating options (branches) from a specific protocol to a next protocol.

The X-ray CT apparatus 1 according to the first embodiment performs a generation process of generating a workflow and an extraction process of extracting a candidate protocol from the workflow. Hereinafter, the generation process and the extraction process will be described in order.

First, the generation process of generating a workflow will be described with reference to FIG. 2. FIG. 2 is a flowchart illustrating a processing procedure of the generation process by the X-ray CT apparatus 1 according to the first embodiment. FIG. 2 will be described with reference to FIG. 3A, FIG. 3B, FIG. 3C, FIG. 3D, FIG. 4A, FIG. 4B, FIG. 4C, and FIG. 4D. Note that the following processing procedure is merely an example and is not limited to the processing procedure of FIG. 2. For example, the processing content and order can be appropriately changed as long as no contradiction exists in the processing content.

As illustrated in FIG. 2, at step S101, the processing circuitry 44 of the X-ray CT apparatus 1 determines whether a processing timing is reached. For example, when an instruction for starting the generation process is received from a user, the processing circuitry 44 determines that the processing timing is reached (Yes at step S101) and starts the generation process of FIG. 2. Note that the processing circuitry 44 does not determine that the processing timing is reached (No at step S101) and does not start the generation process of FIG. 2 until the instruction for starting the generation process is received from the user.

When it is determined that the processing timing is reached (Yes at step S101), the generation function 445 reads history information from the memory 41 at step S102. The history information is, for example, information including information (order information) indicating a protocol executed next to a specific protocol and the result of a scan by each protocol. Note that the order information includes identification information (protocol identification information) indicating the specific protocol and identification information indicating the protocol executed next to the specific protocol.

The history information will be described with reference to FIG. 3A, FIG. 3B, FIG. 3C, and FIG. 3D. FIG. 3A, FIG. 3B, FIG. 3C, and FIG. 3D are diagrams for explaining the history information according to the first embodiment. Note that the history information illustrated in FIG. 3A, FIG. 3B, FIG. 3C, and FIG. 3D is merely an example and is not limited to the content illustrated in the drawings.

Figure 3A:
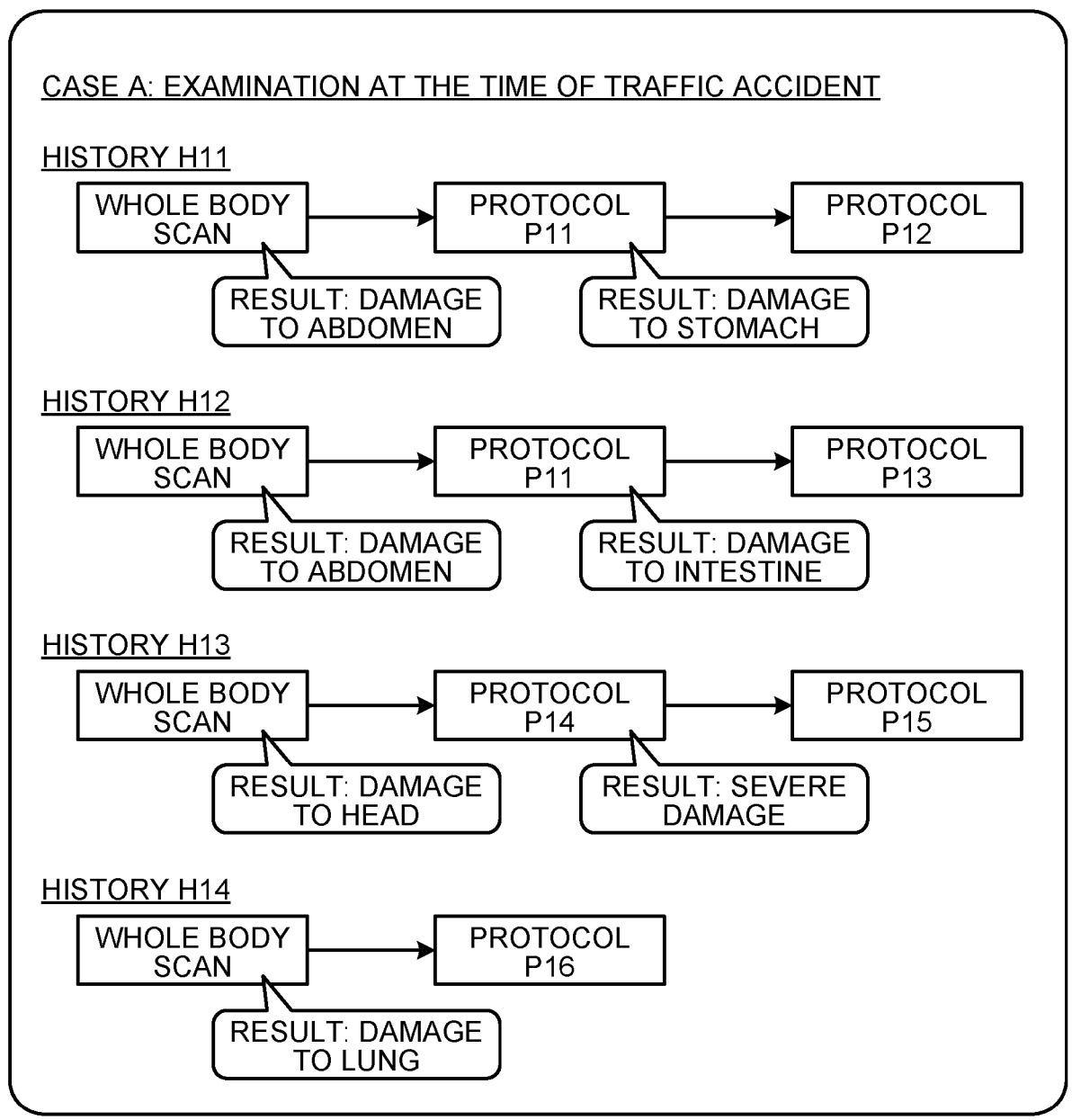
FIG. 3A to 3D are diagrams for explaining history information according to the first embodiment.

FIG. 3A illustrates history H11, history H12, history H13, and history H14 as history information related to case A "examination at the time of traffic accident". In FIG. 3A, "whole body scan" is identification information of a protocol for imaging the whole body of a subject. In the examination at the time of traffic accident, a damage site is roughly searched starting from the "whole body scan" and is specified by executing a detailed scan step by step while narrowing an imaging range.

The history H11 includes order information indicating that protocols "whole body scan", "protocol P11", and "protocol P12" have been executed in order. Furthermore, the history H11 includes information "damage to the abdomen" as a result of the "whole body scan". Furthermore, the history H11 includes information "damage to the stomach" as a result of the "protocol P11". Note that the "protocol P11" is identification information of a protocol for scanning the abdomen, and the "protocol P12" is identification information of a protocol for scanning the stomach. Furthermore, the result of the finally executed protocol (protocol P12) may not be stored.

The history H12 includes order information indicating that protocols "whole body scan", "protocol P11", and "protocol P13" have been executed in order. Furthermore, the history H12 includes information "damage to the abdomen" as a result of the "whole body scan". Furthermore, the history H12 includes information "damage to the intestine" as a result of the "protocol P11". Note that the "protocol P13" is identification information of a protocol for scanning the intestine.

The history H13 includes order information indicating that protocols "whole body scan", "protocol P14", and "protocol P15" have been executed in order. Furthermore, the history H13 includes information "damage to the head" as a result of the "whole body scan". Furthermore, the history H13 includes information "severe damage" as a result of the "protocol P14". Note that the "severe damage" is, for example, information indicating that a specific part of the head is severely affected. The "protocol P14" is identification information of a protocol for scanning the head, and the "protocol P15" is identification information of a protocol for scanning the specific part of the head.

The history H14 includes order information indicating that protocols "whole body scan" and of "protocol P16" have been executed in order. Furthermore, the history H14 includes information "damage to the lung" as a result of the "whole body scan". Note that the "protocol P16" is identification information of a protocol for scanning the lung.

Figure 3B:
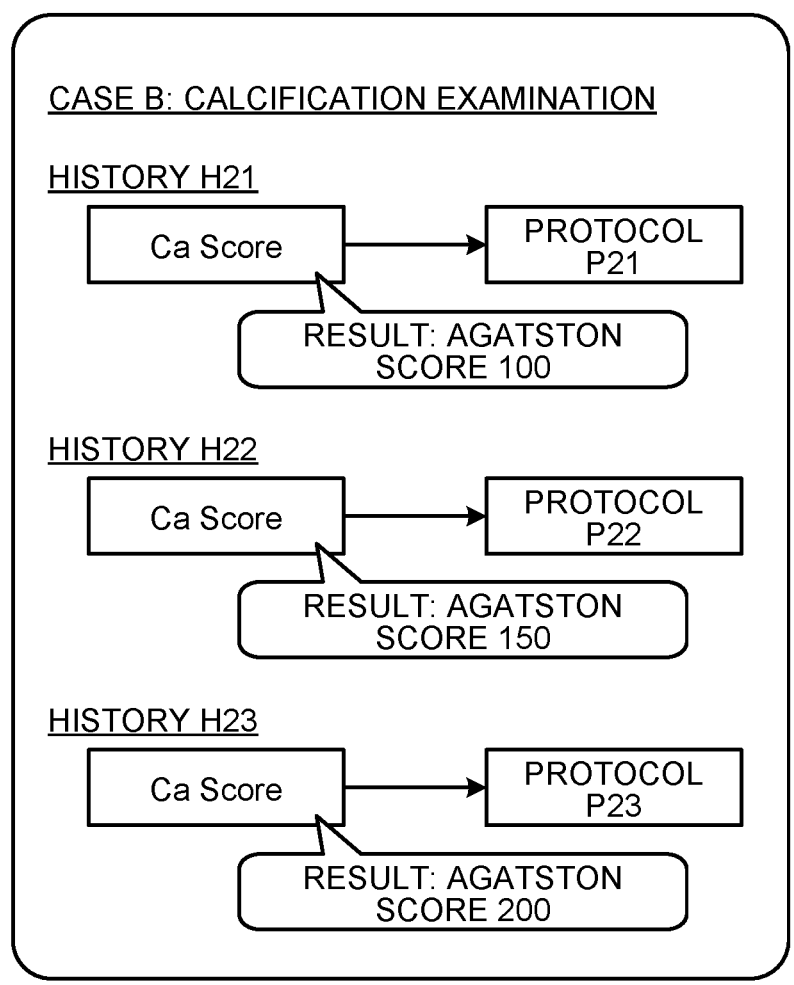

FIG. 3B illustrates history H21, history H22, and history H23 as history information related to case B "calcification examination". In FIG. 3B, "Ca Score" is identification information of a protocol for measuring the calcification of coronary arteries that nourish the heart, and an index value such as "Agatston score" is calculated as a calcification index. In the calcification examination, the calcification of the coronary arteries is measured starting from the "Ca Score" and a next protocol is selected according to the measurement result. Note that "protocol P21", "protocol P22", and "protocol P23" are arbitrary protocols. The history H21 includes order information indicating that protocols "Ca Score" and "protocol P21" have been executed in order. Furthermore, the history H21 includes information "Agatston score 100" as a result of the "Ca Score".

The history H22 includes order information indicating that protocols "Ca Score" and "protocol P22" have been executed in order. Furthermore, the history H22 includes information "Agatston score 150" as a result of the "Ca Score".

The history H23 includes order information indicating that protocols "Ca Score" and "protocol P23" have been executed in order. Furthermore, the history H23 includes information "Agatston score 200" as a result of the "Ca Score".

Figure 3C:
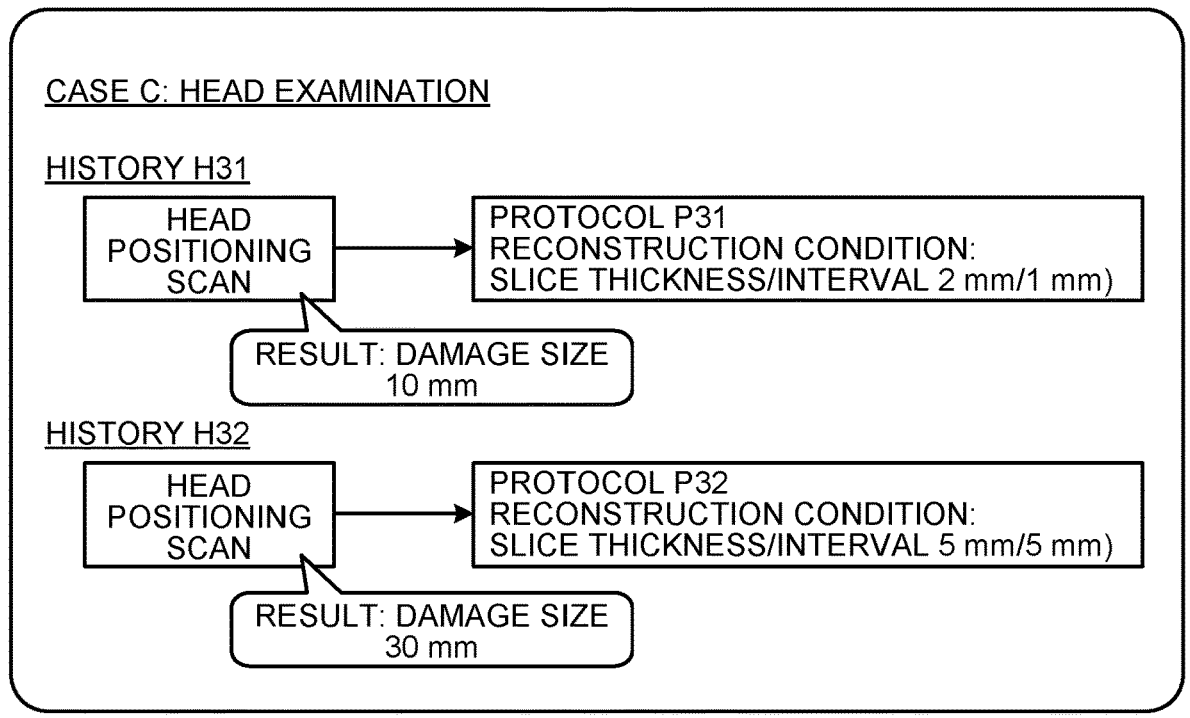

FIG. 3C illustrates history H31 and history H32 as history information related to case C "head examination". In FIG. 3C, "head positioning scan" is identification information of a protocol for confirming a damage site and a damage size in the head. In the head examination of the case C, the damage site and the damage size are specified starting from the "head positioning scan" and a next protocol is selected according to the result.

The history H31 includes order information indicating that protocols "head positioning scan" and "protocol P31" have been executed in order. Furthermore, the history H31 includes information "damage size 10 mm" as a result of the "head positioning scan". Furthermore, the history H31 includes information "slice thickness/interval 2 mm/1 mm" as a reconstruction condition for the "protocol P31".

The history H32 includes order information indicating that protocols "head positioning scan" and "protocol P32" have been executed in order. Furthermore, the history H32 includes information "damage size 30 mm" as a result of the "head positioning scan". Furthermore, the history H32 includes information "slice thickness/interval 5 mm/5 mm" as a reconstruction condition for the "protocol P32".

Figure 3D:
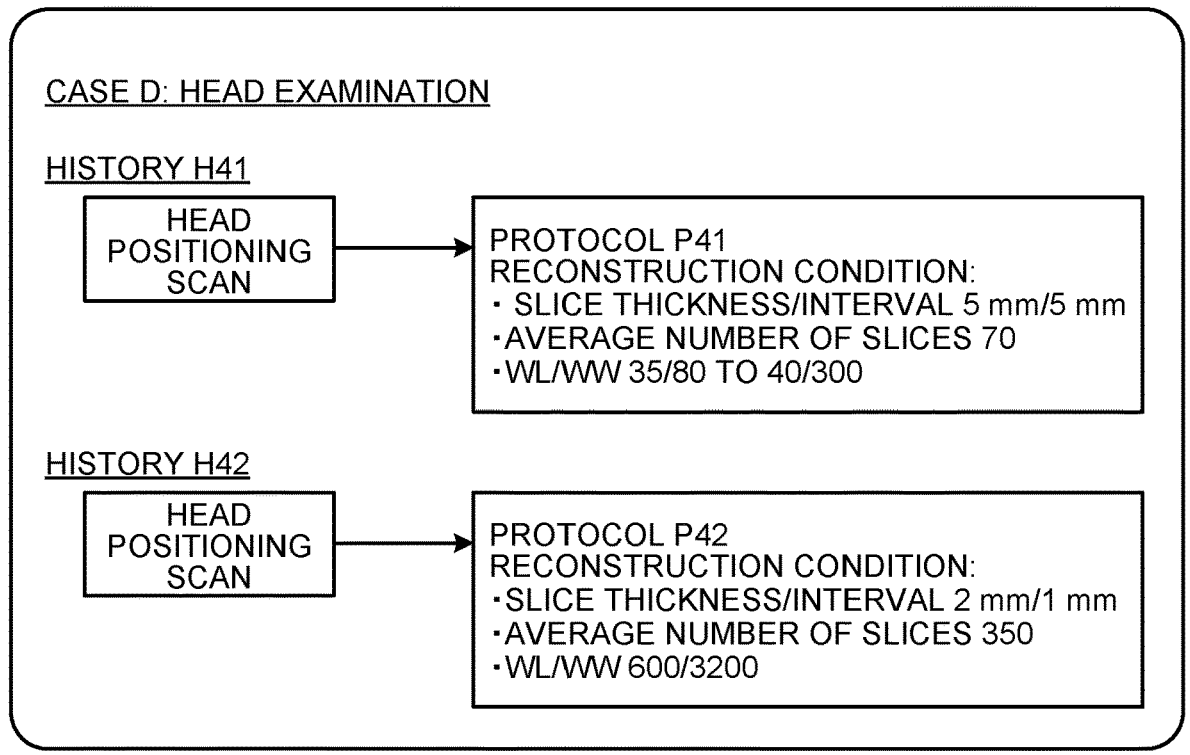

FIG. 3D illustrates history H41 and history H42 as history information related to case D "head examination". In FIG. 3D, "head positioning scan" is identification information of a protocol for confirming a damage site and a damage size in the head. In the head examination of the case D, the "head positioning scan" is used as a starting point and a next protocol is selected according to the result.

The history H41 includes order information indicating that protocols "head positioning scan" and "protocol P41" have been executed in order. Furthermore, the history H41 includes information "slice thickness/interval 5 mm/5 mm", "average number of slices 70", and "WL/WW 35/80 to 40/300" as reconstruction conditions for the "protocol P41".

The history H42 includes order information indicating that protocols "head positioning scan" and "protocol P42" have been executed in order. Furthermore, the history H42 includes information "slice thickness/interval 2 mm/1 mm", "average number of slices 350", and "WL/WW 600/3200" as reconstruction conditions for the "protocol P42".

In this way, the generation function 445 reads, for example, a plurality of history information having a common starting protocol from the memory 41. Note that the history information is appropriately collected at the stage when a scan by each protocol has been executed, for example, and is stored in advance in a predetermined storage device (for example, the memory 41 and the like).

Note that the history information illustrated in FIG. 3A to FIG. 3D is merely an example and is not limited to the content illustrated in the drawings. For example, in FIG. 3A to FIG. 3D, the cases where a user designates in advance items (damage site, Agatston score, damage size, and the like) of the scan results to be used in a workflow generation process and stores only the designated items, have been described; however, embodiments are not limited thereto. For example, the memory 41 may store all recordable items among the scan results as history information.

Furthermore, the items (damage site, Agatston score, damage size, and the like) of the scan results illustrated in FIG. 3A to FIG. 3D may be information output from an analysis application that automatically analyzes medical images and outputs various scan results, or Information (operation history information) input by a user.

Furthermore, in the examples of FIG. 3C and FIG. 3D, the cases where the history information includes the reconstruction conditions have been described; however, embodiments are not limited thereto. For example, the history information may not include the reconstruction conditions. Since the reconstruction conditions for the respective protocols are stored in a predetermined storage device (for example, the memory 41) as one of the items of the respective protocols, the reconstruction conditions can be achieved even though the reconstruction conditions are not included in the history information.

Referring not back to the description of FIG. 2, at step S103, the generation function 445 generates workflows on the basis of the history information. For example, the generation function 445 generates workflows by specifying the result of a scan before each protocol is executed and using the result of a specified scan as a selection condition for each protocol.

Workflows will be described with reference to FIG. 4A, FIG. 4B, FIG. 4C, and FIG. 4D. FIG. 4A, FIG. 4B, FIG. 4C, and FIG. 4D are diagrams for explaining workflows according to the first embodiment. Note that the workflows illustrated in FIG. 4A, FIG. 4B, FIG. 4C, and FIG. 4D are merely examples and are not limited to the content illustrated in the drawings.

Figure 4A:
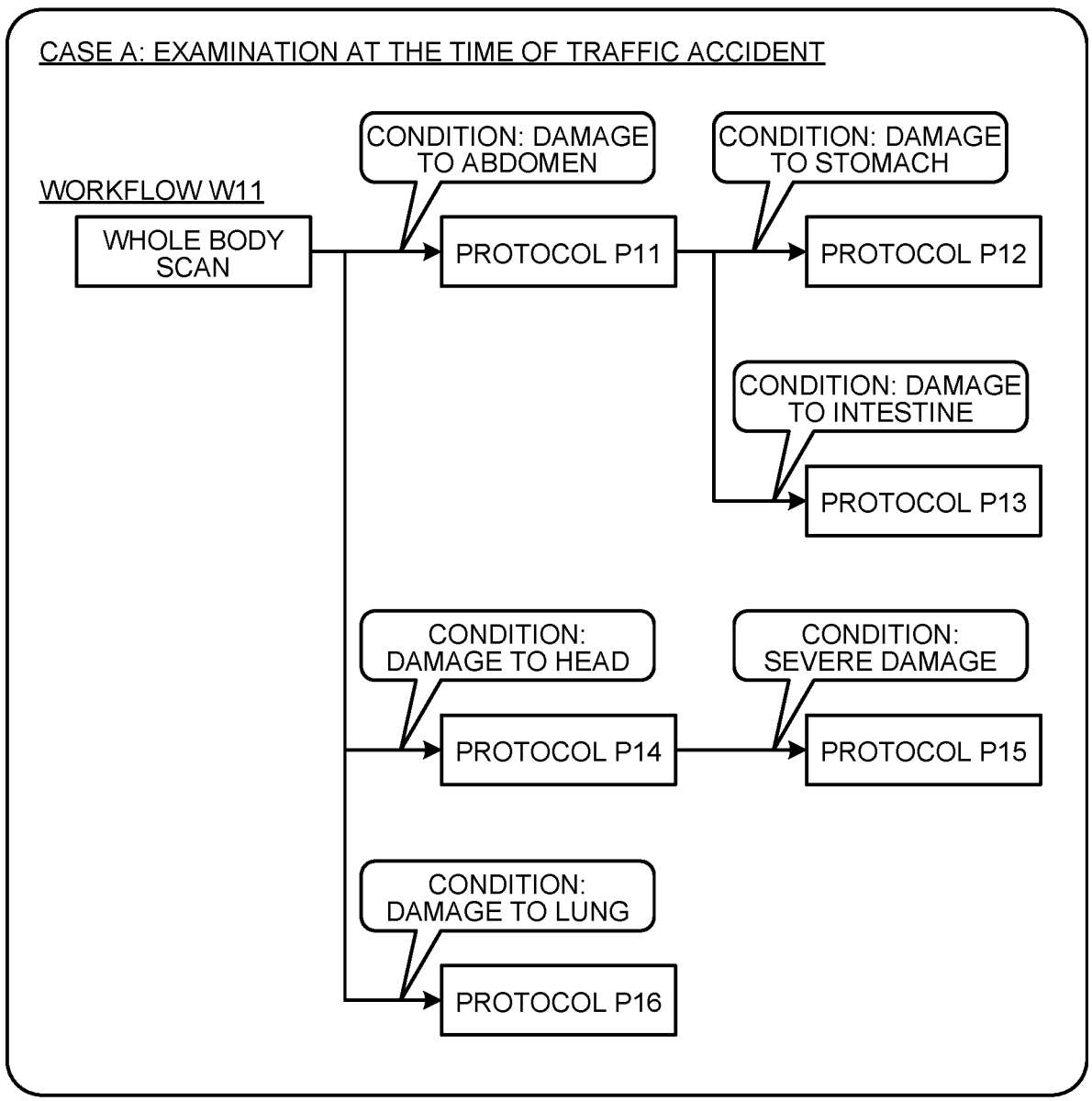
FIG. 4A to 4D are diagrams for explaining workflows according to the first embodiment.

For example, in FIG. 4A, the generation function 445 generates a workflow W11 on the basis of the history H11, the history H12, the history H13, and the history H14 of the case A illustrated in FIG. 3A. Specifically, the generation function 445 refers to the history H11, the history H12, the history H13, and the history H14, and specifies each identification information of the "protocol P11", the "protocol P14", and the "protocol P16" as protocols executed next to the "whole body scan". Furthermore, the generation function 445 specifies the information "damage to the abdomen", which is the result of the "whole body scan" before the "protocol P11" is executed, as a selection condition for the "protocol P11". Furthermore, the generation function 445 specifies the information "damage to the head", which is the result of the "whole body scan" before the "protocol P14" is executed, as a selection condition for the "protocol P14". Furthermore, the generation function 445 specifies the information "damage to the lung", which is the result of the "whole body scan" before the "protocol P16" is executed, as a selection condition for the "protocol P16". Then, the generation function 445 generates the workflow W11 by correlating the identification information, the order information, and the selection conditions for the respective protocols. Since a process of adding the "protocol P12", the "protocol P13", and the "protocol P15" to the workflow W11 is the same as the process described above, description thereof will be omitted.

Figure 4B:
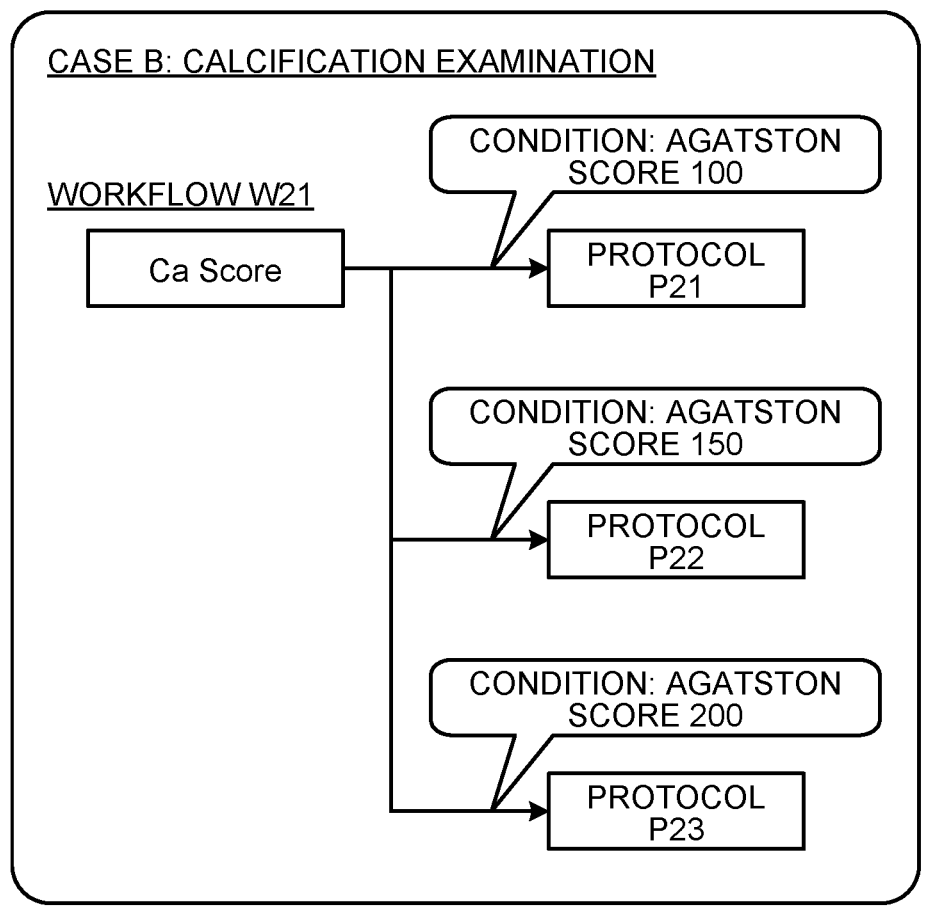

In FIG. 4B, the generation function 445 generates a workflow W21 on the basis of the history H21, the history H22, and the history H23 of the case B illustrated in FIG. 3B. Specifically, the generation function 445 refers to the history H21, the history H22, and the history H23, and specifies each identification information of the "protocol P21", the "protocol P22", and the "protocol P23" as protocols executed next to the "Ca Score". Furthermore, the generation function 445 specifies the information "Agatston score 100", which is the result of the "Ca Score" before the "protocol P21" is executed, as a selection condition for the "protocol P21". Furthermore, the generation function 445 specifies the information "Agatston score 150", which is the result of the "Ca Score" before the "protocol P22" is executed, as a selection condition for the "protocol P22". Furthermore, the generation function 445 specifies the information "Agatston score 200", which is the result of the "Ca Score" before the "protocol P23" is executed, as a selection condition for the "protocol P23". Then, the generation function 445 generates the workflow W21 by correlating the identification information, the order information, and the selection conditions for the respective protocols.

Note that when the selection condition includes an index value, a value matching the selection condition may not be obtained. Therefore, when the selection condition includes the index value, the numerical range of the selection condition may be set on the basis of the value of the scan result. For example, in the example of FIG. 4B, the selection condition for the "protocol P21" may be set to "less than Agatston score 125", the selection condition for the "protocol P22" may be set to "Agatston score 125 or more" and less than Agatston score 175", and the selection condition for the "protocol P23" may be set to "Agatston score 175 or more".

Figure 4C:
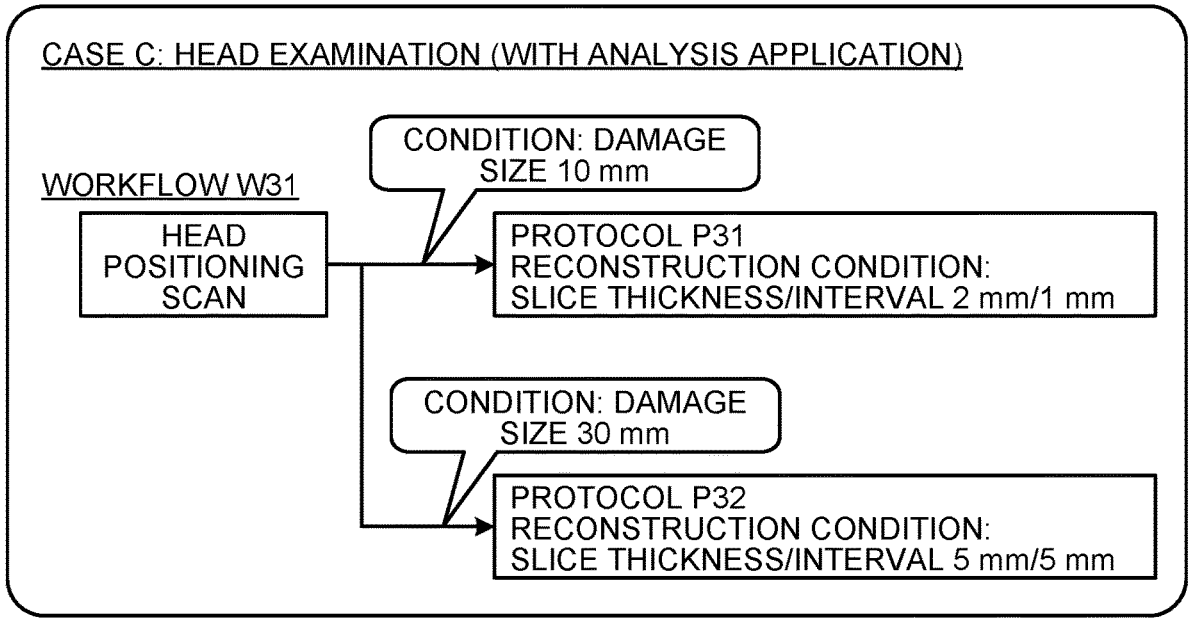

Furthermore, in FIG. 4C, the generation function 445 generates a workflow W31 on the basis of the history H31 and the history H32 of the case C illustrated in FIG. 3C. Specifically, the generation function 445 refers to the history H31 and the history H32, and specifies each identification information of the "protocol P31" and the "protocol P32" as protocols executed next to the "head positioning scan". Furthermore, the generation function 445 specifies the information "damage size 10 mm", which is the result of the "head positioning scan" before the "protocol P31" is executed, as a selection condition for the "protocol P31". Furthermore, the generation function 445 specifies the information "damage size 30 mm", which is the result of the "head positioning scan" before the "protocol P32" is executed, as a selection condition for the "protocol P32". Furthermore, the generation function 445 specifies the "slice thickness/interval 2 mm/1 mm" as a reconstruction condition for the "protocol P31". Furthermore, the generation function 445 specifies the "slice thickness/interval 5 mm/5 mm" as a reconstruction condition for the "protocol P32". Then, the generation function 445 generates the workflow W31 by correlating the identification information, the order information, the selection conditions, and the reconstruction conditions for the respective protocols.

Figure 4D:
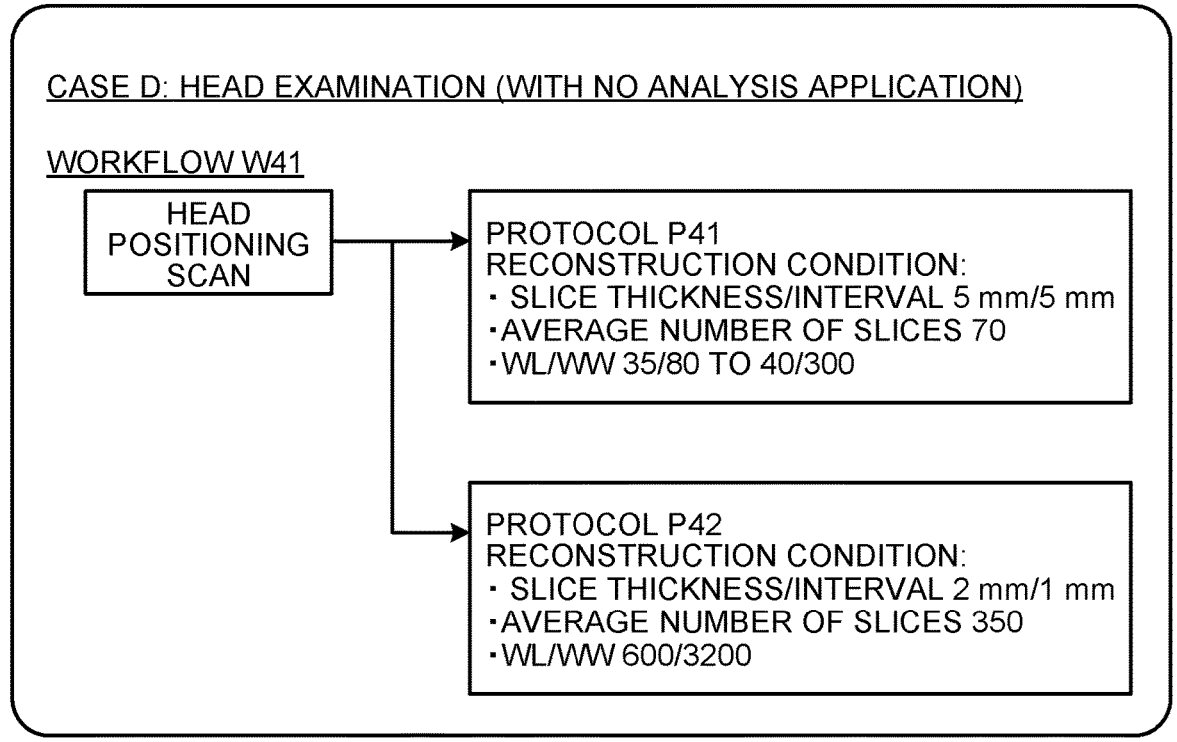

Furthermore, in FIG. 4D, the generation function 445 generates a workflow W41 on the basis of the history H41 and the history H42 of the case D illustrated in FIG. 3D. Specifically, the generation function 445 refers to the history H41 and the history H42, and specifies each identification information of the "protocol P41" and the "protocol P42" as protocols executed next to the "head positioning scan". Furthermore, the generation function 445 specifies the "slice thickness/interval 5 mm/5 mm", "average number of slices 70", and "WL/WW 35/80 to 40/300" as reconstruction conditions for the "protocol P41". Furthermore, the generation function 445 specifies the "slice thickness/interval 2 mm/1 mm", "average number of slices 350", and "WL/WW 600/3200" as reconstruction conditions for the "protocol P42". Then, the generation function 445 generates the workflow W41 by correlating the identification information, the order information, and the reconstruction conditions for the respective protocols. Note that in the example of FIG. 4D, the workflow W41 does not include selection condition.

In this way, the generation function 445 generates the workflows, for example, on the basis of the history information read from the memory 41. Note that the generation function 445 may not simultaneously generate the workflows W11, W21, W31, and W41 illustrated in FIG. 4A to FIG. 4D. For example, the generation function 445 can read a plurality of history information having a common starting protocol, and generate a workflow starting from the protocol by using the read history information.

Furthermore, in the examples of FIG. 4C and FIG. 4D, the cases where the workflow includes the reconstruction conditions have been described; however, embodiments are not limited thereto. For example, the workflow may not include the reconstruction conditions. Since the reconstruction conditions of the respective protocols are stored in a predetermined storage device (for example, the memory 41) as one of the items of the respective protocols, the reconstruction conditions can be achieved even though the reconstruction conditions are not included in the workflow.

Referring not back to the description of FIG. 2, at step S104, the output control function 447 stores the workflows in the memory 41. For example, the output control function 447 stores the workflows W11, W21, W31, and W41 generated by the generation function 445 in the memory 41. Then, the processing circuitry 44 ends the generation process.

Figure 5:
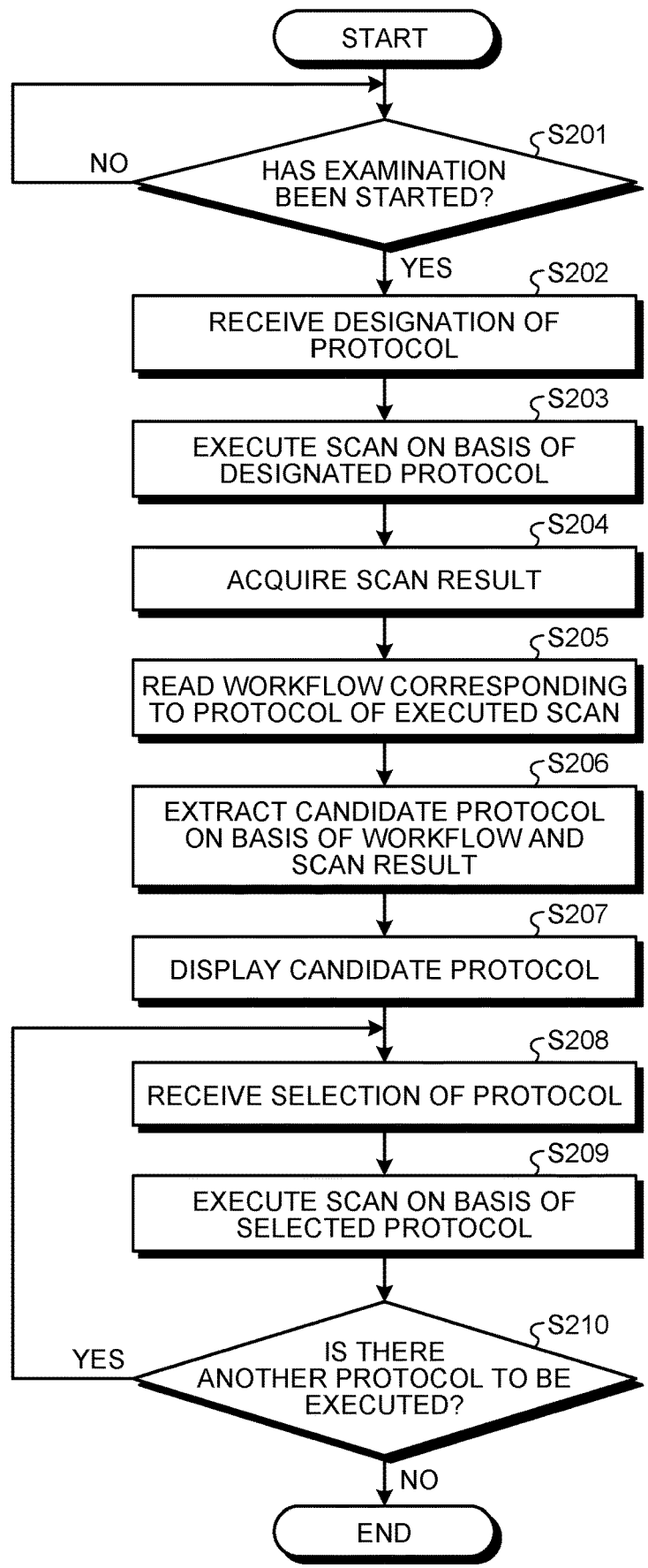
FIG. 5 is a flowchart illustrating a processing procedure of an extraction process by the X-ray CT apparatus according to the first embodiment.

Next, the extraction process of extracting a candidate protocol from a workflow will be described with reference to FIG. 5. FIG. 5 is a flowchart illustrating a processing procedure of the extraction process by the X-ray CT apparatus 1 according to the first embodiment. FIG. 5 will be described with reference to FIG. 6A, FIG. 6B, FIG. 6C, FIG. 6D, FIG. 6E, and FIG. 6F. Note that the following processing procedure is merely an example and is not limited to the processing procedure of FIG. 5. For example, the processing content and order can be appropriately changed within a range in which no contradiction exists in the processing content.

As illustrated in FIG. 5, at step S201, the processing circuitry 44 of the X-ray CT apparatus 1 determines whether an examination has been started. For example, when the examination has been started (Yes at step S201), the processing circuitry 44 starts the process of FIG. 5. Note that the processing circuitry 44 does not start the process of FIG. 5 until the examination is started (No at step S201).

When the examination has been started (Yes at step S201), the system control function 441 receives the designation of a protocol at step S202. For example, when a user designates the protocol "whole body scan", the system control function 441 receives the designation of the protocol "whole body scan".

Note that the number of protocols that are designated here is basically 1, but a plurality of protocols may be designated. For example, a user designates information, which indicates two protocols "Ca Score" and "protocol P21" as protocols to be executed in the examination, and an order in which the "protocol P21" is executed after the "Ca Score". With this, the system control function 441 receives the information, which indicates two protocols "Ca Score" and "protocol P21", and order information in which the "protocol P21" is executed after the "Ca Score".

Subsequently, at step S203, the system control function 441 executes a scan on the basis of the designated protocol.

For example, when the "whole body scan" is designated, the system control function 441 executes the "whole body scan". Furthermore, when a plurality of protocols are designated, the system control function 441 executes a scan of a first protocol (for example, "Ca Score").

Then, at step S204, the extraction function 446 acquires a scan result. For example, the extraction function 446 acquires the scan result by inputting a medical image obtained by the scan into an analysis application.

For example, in the case of the case A, the extraction function 446 inputs a medical image obtained by the "whole body scan" into an analysis application for automatically specifying a damage part, thereby acquiring information on a damage part, such as "damage to the abdomen" and "damage to the intestine", as a scan result.

Furthermore, in the case of the case B, the extraction function 446 inputs a medical image obtained by the "Ca Score" into an analysis application for automatically measuring an Agatston score, thereby acquiring a value, such as "Agatston score 100", as a scan result.

Note that the type of the analysis application used here is preferably correlated with a prior scan protocol. For example, it is preferable to correlate an analysis application for automatically specifying a damage part with the "whole body scan".

Furthermore, when there are a plurality of analysis applications correlated with a specific protocol, it is preferable to narrow down the analysis applications from information and the like related to an examination. For example, an analysis application for automatically specifying a damage part and an analysis application for detecting a tumor from a whole body image may be correlated with the "whole body scan". Therefore, in the case of the case A (traffic accident), the extraction function 446 can selectively execute an analysis application for specifying a damage part, instead of detecting a tumor, by receiving an input indicating a "traffic accident" from a user.

Furthermore, in the above description, the case of using the analysis application has been described; however, embodiments are not limited thereto. For example, when the analysis application is not used, information on a damage part can also be acquired by the input of a user who has browsed a medical image obtained by the "whole body scan".

Furthermore, for example, the extraction function 446 can also acquire, as a scan result, information on an operation performed by a user according to a result of a scan. For example, when a parameter is changed by the input of a user who has browsed a medical image obtained by a scan, the extraction function 446 can also acquire the operation history as a scan result.

Then, at step S205, the extraction function 446 reads a workflow corresponding to a protocol of the executed scan. For example, when the "whole body scan" is executed by the system control function 441, the extraction function 446 reads, from the memory 41, the workflow W11 starting from the "whole body scan". Furthermore, when the "Ca Score" is executed by the system control function 441, the extraction function 446 reads, from the memory 41, the workflow W21 starting from the "Ca Score".

Then, at step S206, the extraction function 446 extracts a candidate protocol on the basis of the workflow and the scan result. For example, the extraction function 446 reads a workflow starting from the protocol of the executed scan among the workflows stored in the memory 41. Then, the extraction function 446 extracts the identification information of a candidate protocol corresponding to a selection condition corresponding to the result of the executed scan among a plurality of candidate protocols included in the read workflow. Then, the extraction function 446 outputs the identification information of the extracted candidate protocol to the output control function 447.

The extraction process of the extraction function 446 will be described with reference to FIG. 6A, FIG. 6B, FIG. 6C, FIG. 6D, FIG. 6E, and FIG. 6F. FIG. 6A, FIG. 6B, FIG. 6C, FIG. 6D, FIG. 6E, and FIG. 6F are diagrams for explaining the extraction process of the extraction function 446 according to the first embodiment. Note that the recommended workflows illustrated in FIG. 6A, FIG. 6B, FIG. 6C, FIG. 6D, FIG. 6E, and FIG. 6F are merely examples and are not limited to the content illustrated in the drawings.

Figure 6A:
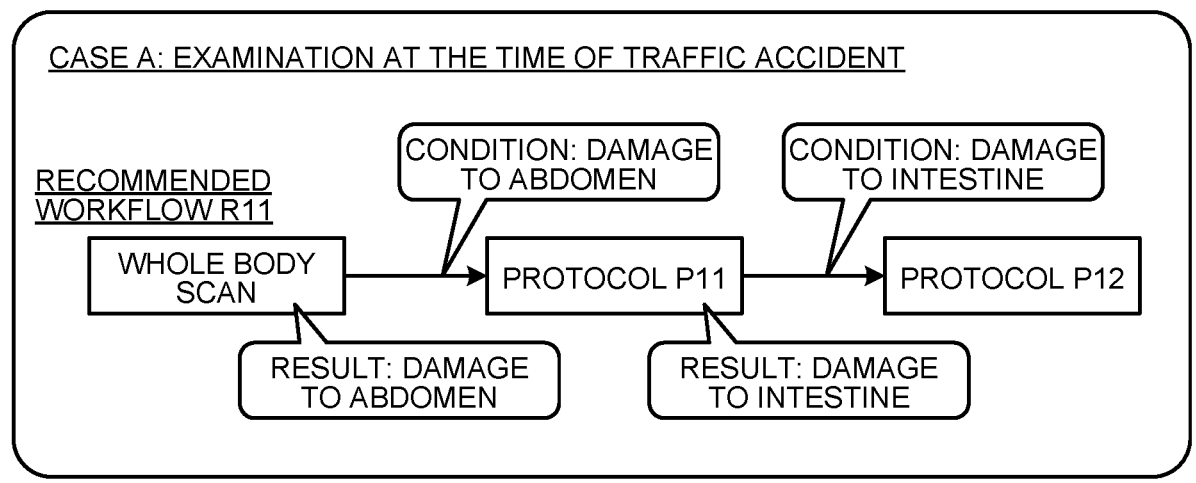

FIG. 6A describes a case where the scan result "damage to the abdomen" is obtained in the "whole body scan" of the case A "examination at the time of traffic accident". In such a case, the extraction function 446 reads the workflow W11 (see FIG. 4A) starting from the "whole body scan" among the workflows stored in the memory 41. Then, the extraction function 446 extracts the "protocol P11" with the scan result "damage to the abdomen" as a selection condition from among the three candidate protocols "protocol P11", "protocol P14", and "protocol P16" that can be executed next to the "whole body scan" in the workflow W11. Then, the extraction function 446 outputs the identification information "protocol P11" of the extracted candidate protocol to the output control function 447 as a recommended workflow R11.

Furthermore, in FIG. 6A, when the "protocol P11" is further executed, the extraction function 446 extracts a candidate protocol, which can be executed next, on the basis of the scan result of the "protocol P11". For example, a case where the scan result "damage to the intestine" is obtained in the "protocol P11" will be described. In such a case, the extraction function 446 extracts the "protocol P13" with the scan result "damage to the intestine" as a selection condition from among the two candidate protocols "protocol P12" and "protocol P13" that can be executed next to the "protocol P11" in the workflow W11. Then, the extraction function 446 outputs the identification information "protocol P13" of the extracted candidate protocol to the output control function 447 as the recommended workflow R11.

Figure 6B:
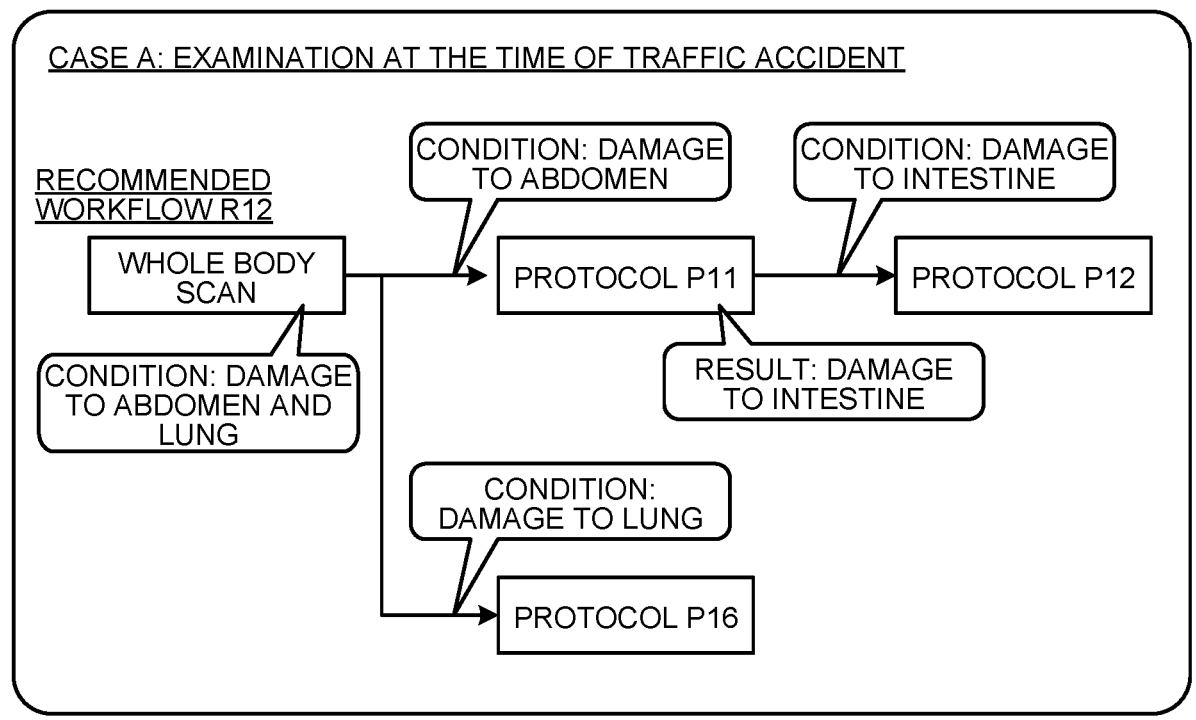

FIG. 6B describes a case where the scan results "damage to the abdomen" and "damage to the lung" are obtained in the "whole body scan" of the case A "examination at the time of traffic accident". In such a case, the extraction function 446 reads the workflow W11 (see FIG. 4A) starting from the "whole body scan" among the workflows stored in the memory 41. Then, the extraction function 446 extracts the "protocol P11" with the scan result "damage to the abdomen" as a selection condition and the "protocol P16" with the scan result "damage to the lung" as a selection condition from among the three candidate protocols "protocol P11", "protocol P14", and "protocol P16" that can be executed next to the "whole body scan" in the workflow W11. Then, the extraction function 446 outputs the identification information "protocol P11" and "protocol P16" of the extracted candidate protocols to the output control function 447 as a recommended workflow R12.

In addition, in FIG. 6B, when the "protocol P11" is further executed and the scan result "damage to the intestine" is obtained, the extraction function 446 extracts the "protocol P13" with the scan result "damage to the intestine" as a selection condition. Since this process is the same as the process described in FIG. 6A, description thereof will be omitted.

Figure 6C:
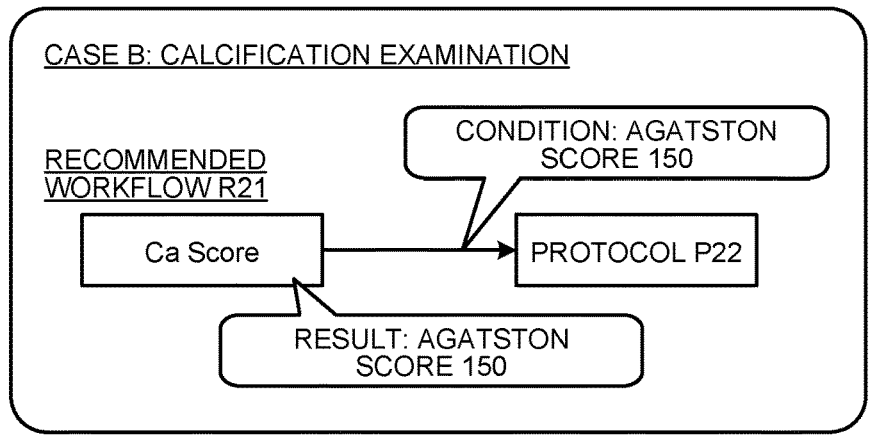

FIG. 6C describes a case where the scan result "Agatston score 150" is obtained in the "Ca Score" of the case B "calcification examination". In such a case, the extraction function 446 reads the workflow W21 (see FIG. 4B) starting from the "Ca Score" among the workflows stored in the memory 41. Then, the extraction function 446 extracts the "protocol P22" with the scan result "Agatston score 150" as a selection condition from among the three candidate protocols "protocol P21", "protocol P22", and "protocol P23" that can be executed next to the "Ca Score" in the workflow W21. Then, the extraction function 446 outputs the identification information "protocol P22" of the extracted candidate protocol to the output control function 447 as a recommended workflow R21.

Figure 6D:
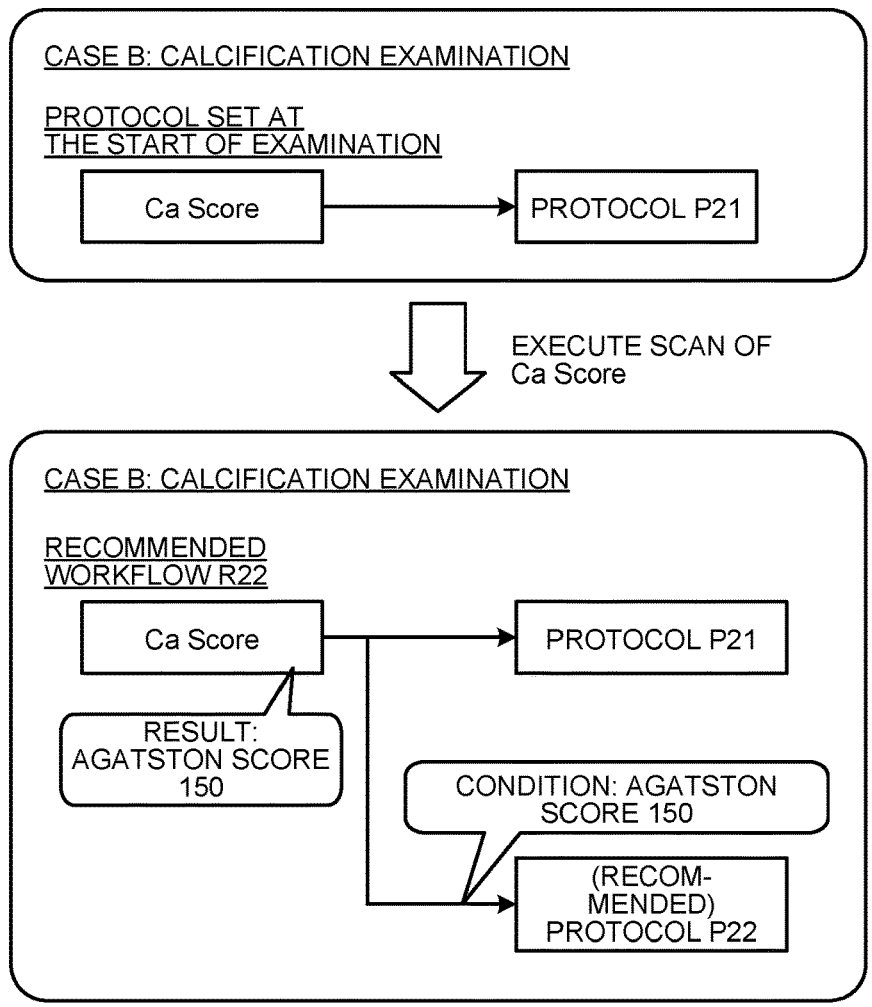

FIG. 6D describes a case where it is preset at the start of examination that the "protocol P21" is executed after the "Ca Score" in the case B "calcification examination". In such a case, when the scan result "Agatston score 150" is obtained, the extraction function 446 reads the workflow W21 (see FIG. 4B) starting from the "Ca Score" among the workflows stored in the memory 41. Then, the extraction function 446 extracts the "protocol P22" with the scan result "Agatston score 150" as a selection condition from among the three candidate protocols "protocol P21", "protocol P22", and "protocol P23" that can be executed next to the "Ca Score" in the workflow W21. Then, the extraction function 446 outputs the identification information "protocol P22" of the extracted candidate protocol to the output control function 447 as a recommended workflow R22.

Note that when the selection condition includes an index value, a value matching the selection condition may not be obtained. Therefore, when the selection condition includes the index value, a candidate protocol with a value close to the value of a scan result as a selection condition may be extracted. For example, when the obtained Agatston score is "190", the extraction function 446 extracts the "protocol P23" because the selection condition "Agatston score 200" of the "protocol P23" is close to "190".

Figure 6E:
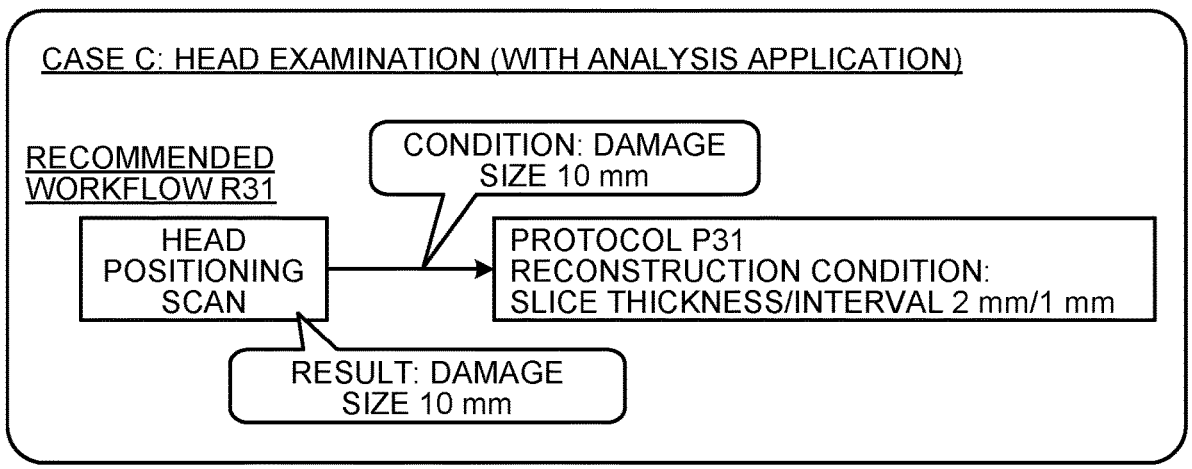

FIG. 6E describes a case where the scan result "damage size 10 mm" is obtained in the "head positioning scan" of the case C "head examination (with analysis application)". In such a case, the extraction function 446 reads the workflow W31 (see FIG. 4C) starting from the "head positioning scan" among the workflows stored in the memory 41. Then, the extraction function 446 extracts the "protocol P31" with the scan result "damage size 10 mm" as a selection condition from among the two candidate protocols "protocol P31" and "protocol P32" that can be executed next to the "head positioning scan" in the workflow W31. Then, the extraction function 446 outputs the identification information "protocol P31" of the extracted candidate protocol to the output control function 447 as a recommended workflow R31.

FIG. 6F describes a case where it is set at the start of examination that the "protocol P41" with the reconstruction condition "WL/WW 35/80" is executed after the "head positioning scan" in the case D "head examination (with no analysis application)". In such a case, the extraction function 446 reads the workflow W41 (see FIG. 4D) starting from the "head positioning scan" among the workflows stored in the memory 41. When no analysis application exists (or when no analysis application works), a user browses a medical image obtained by the "head positioning scan" and considers a next protocol from the conditions of a damage site and the like. As a result of the consideration, when the user changes the "WL/WW 35/80" to the "WL/WW 600/3200" in the reconstruction conditions for the "protocol P41" planned next, the extraction function 446 acquires the operation history (change history) as a scan result. Then, the extraction function 446 extracts the candidate protocol "protocol P42" including the scan result "WL/WW 600/3200" as a reconstruction condition from among the two candidate protocols "protocol P41" and "protocol P42" that can be executed next to the "head positioning scan" in the workflow W41. Then, the extraction function 446 outputs the identification information "protocol P42" of the extracted candidate protocol to the output control function 447 as a recommended workflow R41.

Note that in FIG. 6F, when the "WL/WW 35/80" is changed to the "WL/WW 40/300", the extraction function 446 determines that it is within the range of the reconstruction condition for the "protocol P41" and does not extract the "protocol P42".

In this way, the extraction function 446 extracts candidate protocols on the basis of the workflows and the scan results. Then, the extraction function 446 outputs the identification information of the extracted candidate protocols to the output control function 447.

Note that the aforementioned processing of the extraction function 446 is merely an example and embodiments are not limited thereto. For example, the content illustrated in FIG. 6A to FIG. 6F can be arbitrarily changed as long as no contradiction exists in the processing content.

Then, at step S207, the output control function 447 displays the candidate protocols. For example, the output control function 447 allows the identification information of the candidate protocols extracted by the extraction function 446 to be displayed on the display 42.

For example, the output control function 447 may display the candidate protocols in the formats of the recommended workflows illustrated in FIG. 6A to FIG. 6F, or information arbitrarily selected from the illustrated recommended workflows. In the example of FIG. 6A, the output control function 447 may also display only the recommended protocol "protocol P11". Furthermore, the output control function 447 may select arbitrary information from the "whole body scan" previously executed, the scan result "damage to the abdomen", the selection condition "damage to the abdomen", and the like, and display the selected information, in addition to the recommended protocol "protocol P11".

Furthermore, in the example of FIG. 6D, it is preset at the start of examination that the "protocol P21" is executed after the "Ca Score". In such a case, it is preferable that the output control function 447 highlights the "protocol P22" extracted by the extraction function 446, in addition to the "protocol P21" set in advance. Examples of the highlighting include a case of writing the word "recommended", a case of emphasizing the "protocol P22" by a display form such as a thick line and a marker, a case of relatively emphasizing the "protocol P21" by allowing the "protocol P21" to be discreet by a display form such as increasing the transmittance and applying shadows.

Furthermore, the output control function 447 may display the candidate protocols in the form of the workflows illustrated in FIG. 4A to FIG. 4D. In such a case, the output control function 447 may display the selection conditions of candidate protocols not extracted by the extraction function 446. With this, a user can understand the reason why the non-recommended candidate protocols have not been recommended. For example, in the workflow W11 of FIG. 4A, when the "protocol P11" is extracted and the "protocol P14" and the "protocol P16" are not extracted, a user can understand that "no damage to the head and the lung" and understand that "sites, other than the abdomen, the head, and the lung, are not subjected to damage site analysis by an analysis application".

Note that the output control function 447 can not only allow the workflows to be displayed on the display 42, but also output the workflows in various forms. For example, the output control function 447 can transfer the workflows to an external apparatus, or store the workflows in any recording medium. Note that the workflows stored in any recording medium can be read by any medical image diagnosis apparatus.

Then, at step S208, the system control function 441 receives the selection of a protocol. For example, when the recommended workflow R12 illustrated in FIG. 6B is displayed, a user performs an operation of selecting either the "protocol P11" or the "protocol P16". The system control function 441 receives the candidate protocol selected by the user as a protocol to be executed next.

Note that a user may not select a protocol from the candidate protocols displayed by the output control function 447. For example, when the recommended workflow R11 illustrated in FIG. 6A is displayed, a user may not select the "protocol P11". That is, the user can select any protocol from the protocols stored in the X-ray CT apparatus 1.

Furthermore, the system control function 441 may not receive the selection of a protocol. For example, as illustrated in FIG. 6A, when the number of candidate protocols extracted by the extraction function 446 is 1, the system control function 441 may automatically execute a candidate protocol without receiving a user's operation.

Then, at step S209, the system control function 441 executes a scan on the basis of the selected protocol. For example, when the "protocol P11" is selected, the system control function 441 executes the scan of the "protocol P11".

Then, at step S210, the system control function 441 determines whether there is any other protocol to be executed. For example, in FIG. 6B, the "protocol P11" has been executed, but the "protocol P16" may not be executed. In such a case, the system control function 441 determines that there is another protocol to be executed (Yes at step S210), proceeds to the process of step S208, and receives the selection of an unexecuted protocol.

Furthermore, when a plurality of candidate protocols exist after the protocol of the scan executed at step S209, the system control function 441 proceeds to step S204. For example, as illustrated in FIG. 4A, two protocols "protocol P12" and "protocol P13" may exist after the "protocol P11". In such a case, the system control function 441 executes the "protocol P11" and then proceeds to step S204. Then, the extraction function 446 acquires the scan result of the previously executed "protocol P11" (step S204), and performs the processes after step S205. Since the description of the processes after step S204 is as described above, description thereof will be omitted.

Furthermore, when it is determined that there is no other protocol to be executed (No at step S210), the system control function 441 ends the procedure of FIG. 5.

As described above, in the X-ray CT apparatus 1 according to the first embodiment, the system control function 441 executes a scan on the basis of a protocol designated by a user. The extraction function 446 extracts a candidate protocol to be executed next to the protocol, on the basis of a workflow (branch information), in which identification information indicating each of a plurality of candidate protocols that can be executed starting from a specific protocol and selection conditions for selecting the respective protocols are correlated with each other, and the result of the scan. The output control function 447 outputs an extracted candidate protocol. Consequently, the X-ray CT apparatus 1 can easily select an appropriate protocol.

For example, in accordance with the X-ray CT apparatus 1 according to the first embodiment, a protocol recommended to be executed next is presented to a user on the basis of a workflow and a scan result. Therefore, the user does not have to select a protocol from all the protocols stored in the X-ray CT apparatus 1, so that the workload can be reduced. Furthermore, even though the user is inexperienced or has a different field of specialization, the user can easily select an appropriate protocol.

Furthermore, a workflow is generated and registered separately from an existing protocol. Therefore, in the X-ray CT apparatus 1, the number of protocols to be managed does not increase. Furthermore, the workflow defines the execution order and options of protocols, and does not basically include various information included in each protocol. Therefore, even when some of the conditions of a protocol such as a positioning scan are changed, if only conditions of a protocol to be changed are changed, even though the protocol is read from any workflow, information of the changed protocol is read. Consequently, the X-ray CT apparatus 1 can restrain an increase in the management load.

In the first embodiment, the "whole body scan", the "Ca Score", and the "head positioning scan" have been described as examples of a starting protocol; however, embodiments are not limited thereto. For example, the generation function 445 can generate a workflow starting from any kind of protocol.

Furthermore, in the first embodiment, the case where the extraction process is performed using a workflow has been described; however, embodiments are not limited thereto. An extraction process using no workflow will be described in a third embodiment.

First Modification of First Embodiment

In the first embodiment, the case where a candidate protocol that can be executed next is presented has been described; however, embodiments are not limited thereto. For example, when there is no need to change a protocol, the X-ray CT apparatus 1 can also present a change in a parameter.

For example, the extraction function 446 extracts a change target parameter on the basis of a workflow and a scan result. Then, the output control function 447 outputs the change target parameter.

Figure 7:
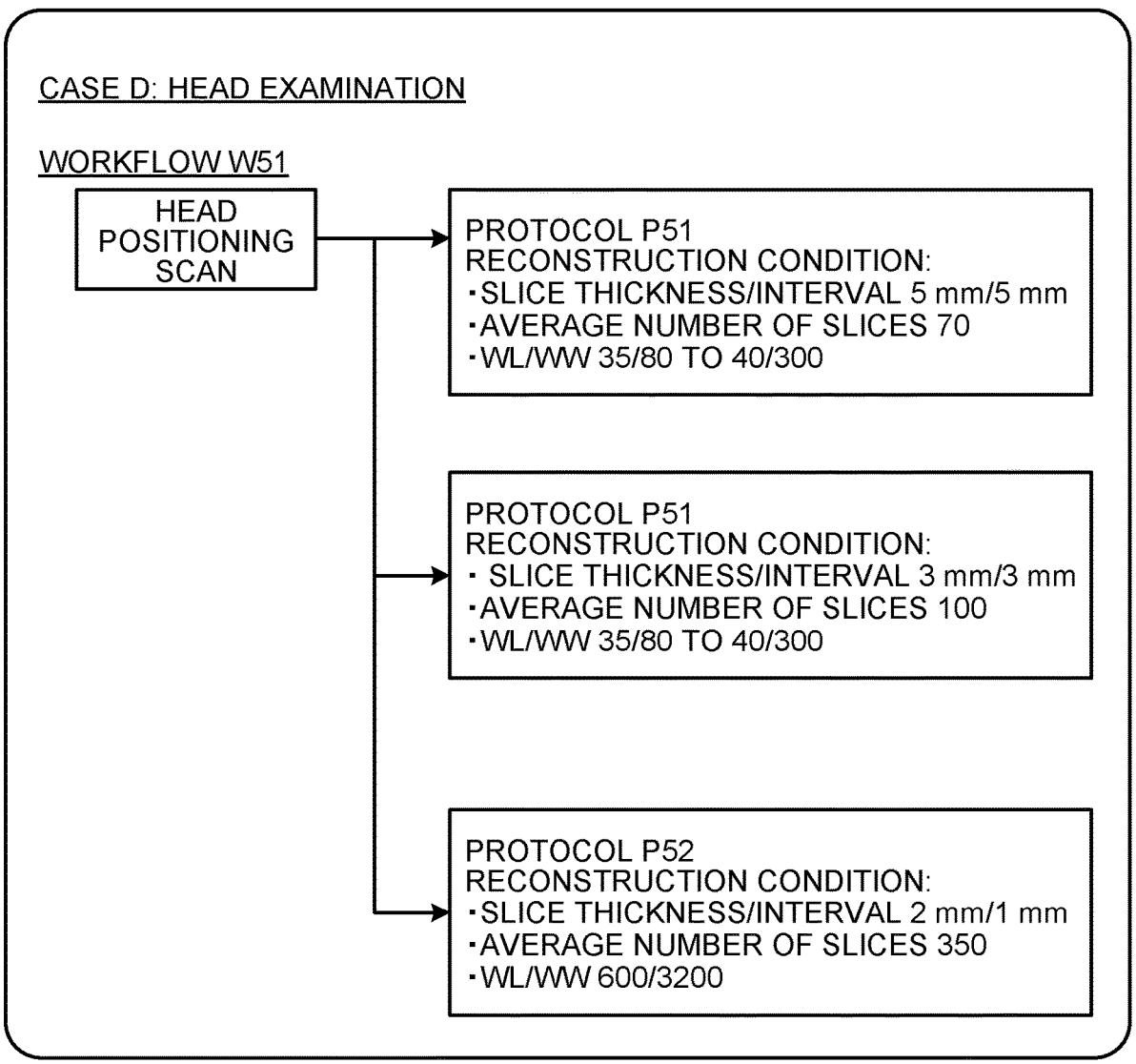
FIG. 7 is a diagram for explaining the extraction process of an extraction function according to a first modification of the first embodiment.

The extraction process of the extraction function 446 according to the first modification of the first embodiment will be described with reference to FIG. 7. FIG. 7 is a diagram for explaining the extraction process of the extraction function 446 according to the first modification of the first embodiment. Note that a workflow illustrated in FIG. 7 is merely an example and is not limited to content illustrated in the drawing.

A workflow W51 illustrated in FIG. 7 stores two protocols "protocol P51" and "protocol P52" as candidate protocols that can be executed after the "head positioning scan". Here, the first "protocol P51" stores "slice thickness/interval 5 mm/5 mm", "average number of slices 70", and "WL/WW 35/80 to 40/300" as reconstruction conditions. Furthermore, the second "protocol P51" stores "slice thickness/interval 3 mm/3 mm", "average number of slices 100", and "WL/WW 35/80 to 40/300" as reconstruction conditions.

In the example illustrated in FIG. 7, it is set at the start of examination that the first "protocol P51" is executed after the "head positioning scan". As a result of browsing a medical image obtained by the "head positioning scan" and considering a next protocol from the conditions of a damage site and the like, a user may change some of the reconstruction conditions for the "protocol P51" planned next. For example, when the user changes the "slice thickness/interval 5 mm/5 mm" to the "slice thickness/interval 3 mm/3 mm", the extraction function 446 acquires this operation history (change history) as a scan result. Then, the extraction function 446 specifies the second "protocol P51" including the "slice thickness/interval 3 mm/3 mm" in the workflow W51. With this, the extraction function 446 determines that the user changes the first "protocol P51" to the second "protocol P51", and extracts a change target parameter "average number of slices 100" that is changed in conjunction with the "slice thickness/interval 3 mm/3 mm". Then, the extraction function 446 outputs the extracted "average number of slices 100" to the output control function 447. Then, the output control function 447 allows the "average number of slices 100" extracted by the extraction function 446 to be displayed on the display 42.

In this way, when some parameters are changed by user input, if there is no need to change a protocol, the X-ray CT apparatus 1 according to the first modification of the first embodiment can extract only a change target parameter and present the extracted parameter to a user.

Note that FIG. 7 has described the case where one parameter is changed in conjunction with a parameter changed by a user has been described; however, embodiments are not limited thereto. For example, even when two parameters are changed in conjunction with a parameter changed by a user, the X-ray CT apparatus 1 may also present a change in a parameter. The number of interacting parameters when presenting a change in a parameter can be controlled by a threshold value. However, since an operation becomes more complicated as the number of parameters changed in conjunction with a parameter changed by a user increases, it is preferable to change a protocol.

Second Modification of First Embodiment

Furthermore, the X-ray CT apparatus 1 can acquire a workflow generated by an external apparatus and use the workflow for examination in the own apparatus (the X-ray CT apparatus 1). Note that the external apparatus is a medical image diagnostic apparatus different from the own apparatus.

For example, in the X-ray CT apparatus 1, the output control function 447 receives a workflow (hereinafter, referred to as an "external flow") generated by an X-ray CT apparatus of another medical institution or facility, and stores the received external flow in the memory 41.

Then, the X-ray CT apparatus 1 reads the external flow stored in the memory 41 and uses the read external flow for examination. For example, when the examination is started, the X-ray CT apparatus 1 performs the extraction process of FIG. 5. In the X-ray CT apparatus 1, the extraction function 446 reads the external flow from the memory 41 and uses the read external flow for an extraction process. Since the extraction process using the external flow is the same as the extraction process using the workflow described above, description thereof will be omitted.

Second Embodiment

For example, the X-ray CT apparatus 1 can change a workflow. The second embodiment will describe a case where a workflow is changed.

Figure 8:
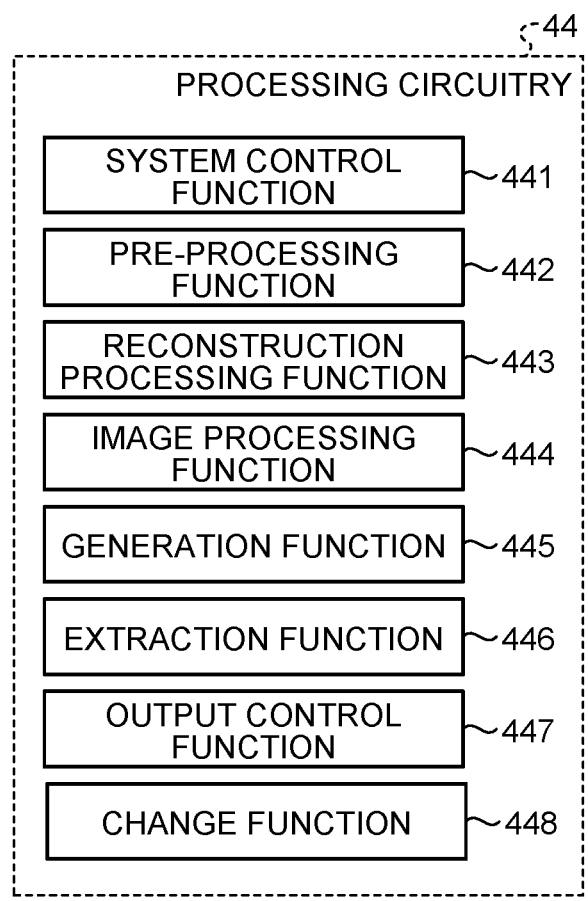
FIG. 8 is a block diagram illustrating an example of a configuration of an X-ray CT apparatus according to a second embodiment.

FIG. 8 is a block diagram illustrating an example of a configuration of an X-ray CT apparatus 1 according to the second embodiment. As illustrated in FIG. 8, in the X-ray CT apparatus 1 according to the second embodiment, the processing circuitry 44 further performs a change function 448. Since the configuration of the X-ray CT apparatus 1 according to the second embodiment is the same as that of the X-ray CT apparatus 1 illustrated in FIG. 1 except that the processing circuitry 44 performs the change function 448, description thereof will be omitted.

In FIG. 8, the change function 448 changes a workflow on the basis of an instruction from a user. For example, the change function 448 reads a change target workflow from the memory 41 and allows the read workflow to be displayed on the display 42. Then, the change function 448 receives a change operation for the workflow from the user on a display screen of the display 42. Then, the change function 448 changes the workflow on the basis of the received change operation. Note that examples of the change operation may include addition, change, and deletion of a candidate protocol, and addition, change, and deletion of a selection condition. Note that the change function 448 is an example of a change unit.

Figure 9A:
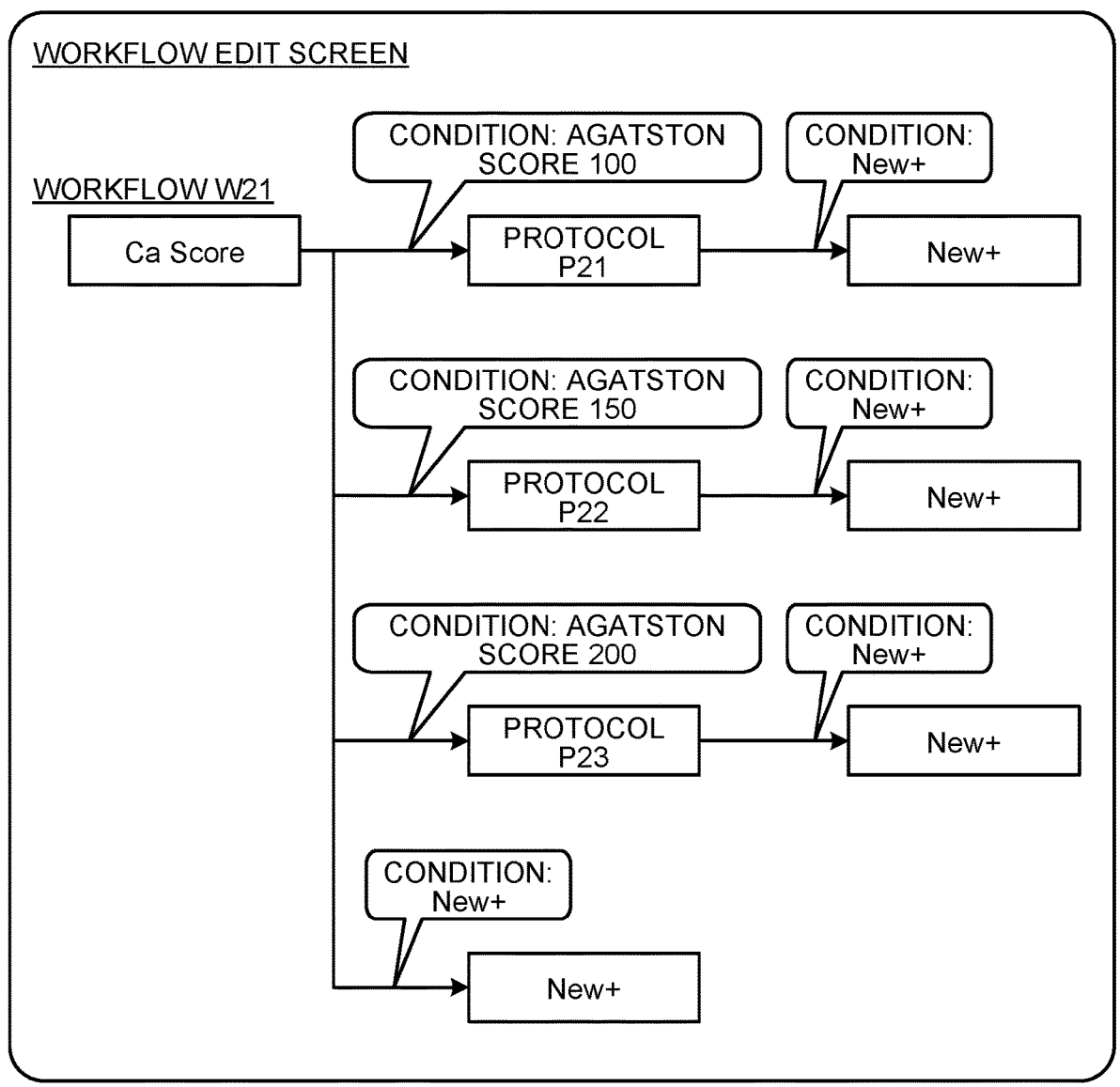
FIGS. 9A and 9B are diagrams for explaining the processing of a change function according to the second embodiment.
Figure 9B:
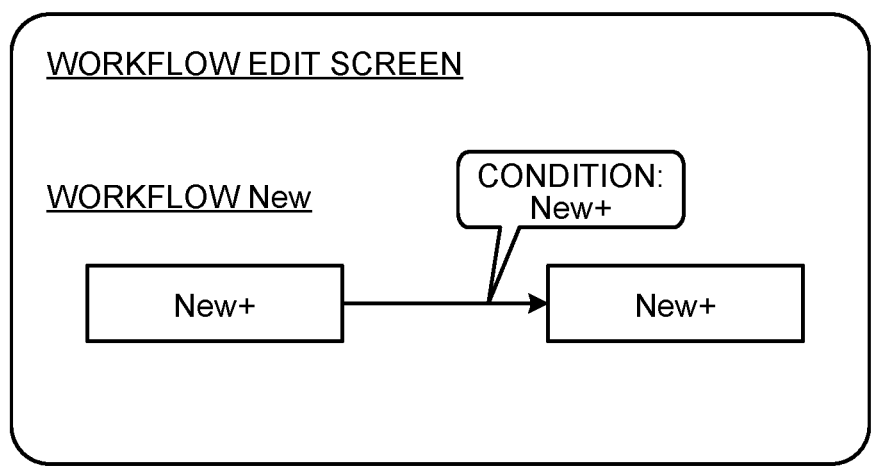

The processing of the change function 448 according to the second embodiment will be described with reference to FIG. 9A and FIG. 9B. FIG. 9A and FIG. 9B are diagrams for explaining the processing of the change function 448 according to the second embodiment. FIG. 9A illustrates a case where the workflow W21 generated in FIG. 4B is changed. Furthermore, FIG. 9B illustrates a case where a workflow is newly generated.

As illustrated in FIG. 9A, the change function 448 allows a workflow edit screen to be displayed on the display 42. On the workflow edit screen, the workflow W21 is displayed as a workflow to be changed. Furthermore, on the workflow edit screen, "New+" is displayed at a display position of a protocol and a display position of a selection condition. By designating the display of the "New+", a user can add a protocol and a selection condition at arbitrary positions.

Furthermore, by designating a registered candidate protocol and a selection condition on the workflow, the registered candidate protocol and the selection condition can be changed or deleted. For example, by designating the "protocol P21", the user can change the designated protocol to another protocol. Furthermore, by designating the deletion of the selection condition "Agatston score 150", the user can delete the designated selection condition.

As illustrated in FIG. 9B, the change function 448 can newly generate a workflow. For example, by selecting the "New+" at the display position of a starting protocol and designating an arbitrary protocol, the user can register the arbitrary protocol as the starting point of the workflow. Furthermore, the user can newly add selection conditions and candidate protocols from the starting protocol.

In this way, the X-ray CT apparatus 1 according to the second embodiment can change a workflow. Note that the X-ray CT apparatus 1 according to the second embodiment can change not only a workflow generated by the own apparatus, but also an external workflow generated by an external apparatus in the same manner. For example, when an external workflow generated by an external apparatus (external facility and the like) is introduced into the own apparatus, it is preferable that the change function 448 changes the introduced external workflow according to the situation of the own apparatus.

First Modification of Second Embodiment

In the second embodiment, the case where a workflow is manually changed has been described; however, a workflow can also be automatically changed.

The change function 448 changes a workflow on the basis of history information and a workflow. For example, the change function 448 changes an external workflow generated by an external apparatus, on the basis of history information stored in the own apparatus.

Figure 10:
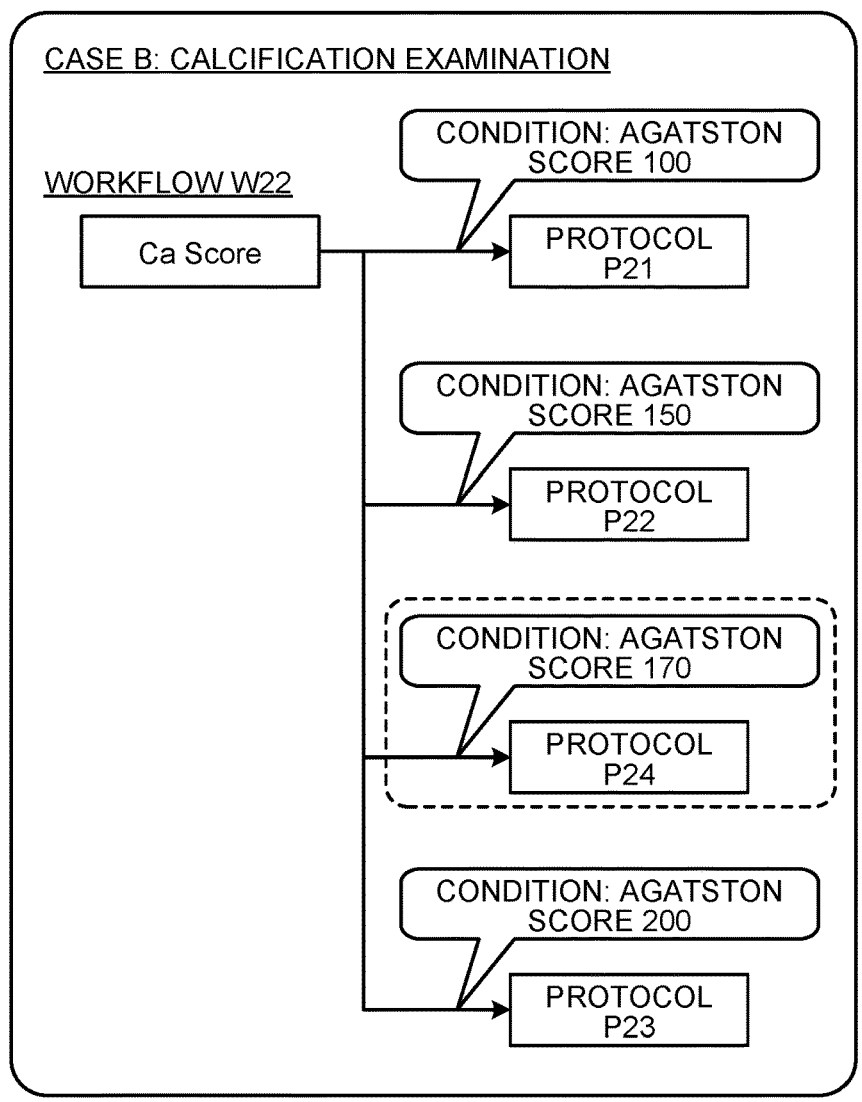
FIG. 10 is a diagram for explaining the processing of a change function according to a first modification of the second embodiment.

The processing of the change function 448 according to the first modification of the second embodiment will be described with reference to FIG. 10. FIG. 10 is a diagram for explaining the processing of the change function 448 according to the first modification of the second embodiment.

FIG. 10 describes a case where the workflow W21 of FIG. 4B is generated by an external apparatus and history H24 exists as history information of the own apparatus. The history H24 includes order information indicating that protocols "Ca Score" and "protocol P24" have been executed in order. Furthermore, the history H24 includes information "Agatston score 170" as a result of the "Ca Score". In such a case, the change function 448 specifies information "Agatston score 170", which is the result of the "Ca Score" before the "protocol P24" is performed, as a selection condition for the "protocol P24".

Then, the change function 448 adds the specified "protocol P24" to the workflow W21 in correlation with the selection condition "Agatston score 170", thereby changing the workflow W21 to a workflow W22 illustrated in FIG. 10. Note that in the workflow W22, a region surrounded by a broken line is a newly added candidate protocol.

In this way, the X-ray CT apparatus 1 according to the first modification of the second embodiment can automatically change a workflow on the basis of history information and a workflow. The automatic change of the workflow is particularly useful when a workflow generated by an external apparatus (external facility and the like) is introduced into the own apparatus as illustrated in FIG. 10.

Note that FIG. 10 has described the case where an external workflow is changed has been described; however, embodiments are not limited thereto, and a workflow generated by the own apparatus can also be changed in the same manner. For example, when new history information is registered, the change function 448 changes a workflow generated by the own apparatus, on the basis of the new history information.

Second Modification of Second Embodiment

Furthermore, the X-ray CT apparatus 1 may present a workflow change plan instead of automatically changing a workflow.

For example, the change function 448 generates a workflow change plan on the basis of history information and a workflow. Then, when the change plan is approved by a user, the change function 448 changes a workflow on the basis of the change plan.

For example, the change function 448 allows the workflow W22 illustrated in the lower figure of FIG. 10 to be displayed on the display 42 as a change plan. In the workflow W22, it is preferable to highlight a portion changed from the workflow W21. A user browses the change plan of the workflow W22 displayed on the display 42 and considers whether to adopt the change plan. When the user approves the change plan, the existing workflow W21 is changed to the new workflow W22. Note that when the change plan is not approved, the change function 448 does not change the workflow.

Third Embodiment

In the above embodiments, the cases where the extraction process is performed using a workflow have been described; however, embodiments are not limited thereto. For example, the X-ray CT apparatus 1 can perform the extraction process by using history information.

That is, in the X-ray CT apparatus 1 according to the third embodiment, the system control function 441 performs a scan on the basis of a protocol selected by a user. The extraction function 446 extracts a candidate protocol, which is executed next, on the basis of history information, which includes information indicating a protocol executed next to a specific protocol and scan results by respective protocols, and the scan results. The output control function 447 outputs the extracted candidate protocol.

Since the configuration of the X-ray CT apparatus 1 according to the third embodiment is the same as that of the X-ray CT apparatus 1 illustrated in FIG. 1, description thereof will be omitted.

Figure 11:
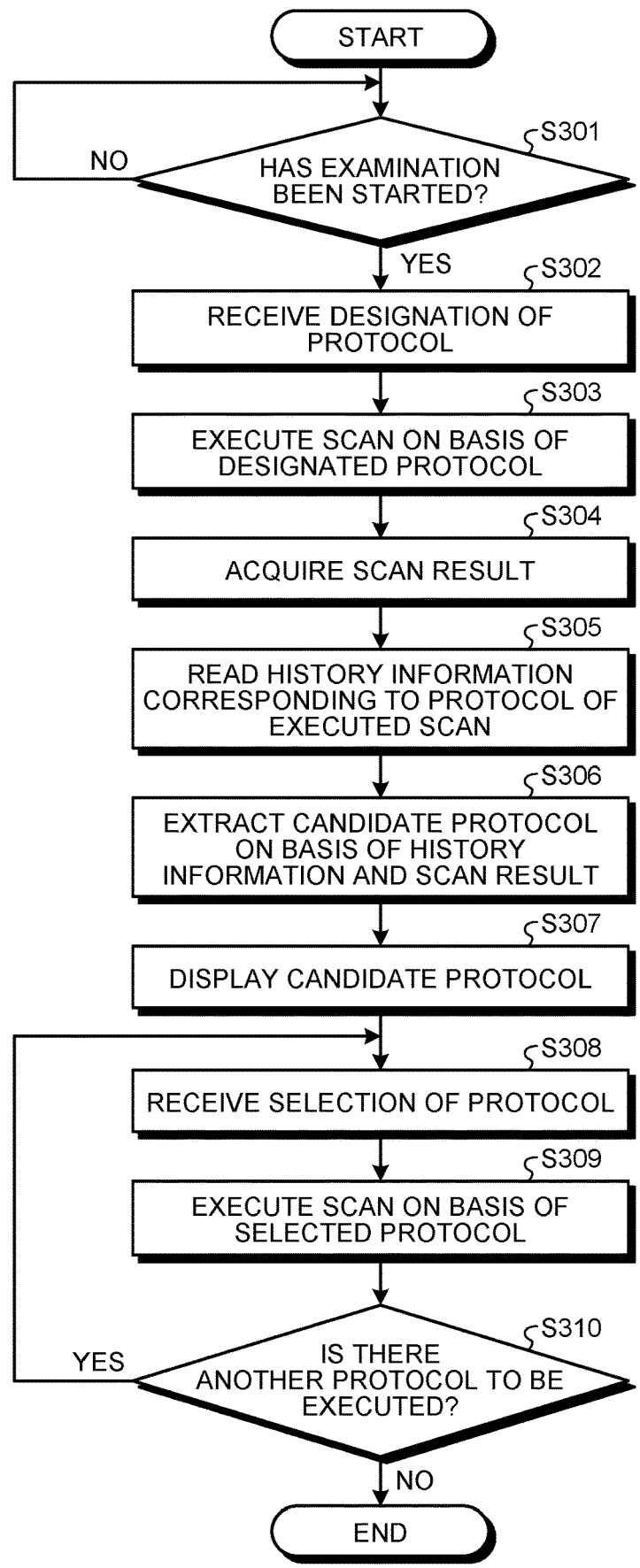
FIG. 11 is a flowchart illustrating a processing procedure of an extraction process by an X-ray CT apparatus according to a third embodiment.

An extraction process of extracting a candidate protocol from history information will be described with reference to FIG. 11. FIG. 11 is a flowchart illustrating a processing procedure of the extraction process by the X-ray CT apparatus 1 according to the third embodiment. Note that the following processing procedure is merely an example and is not limited to the processing procedure of FIG. 11. For example, the processing content and order can be appropriately changed as long as no contradiction exists in the processing content.

Since processes of step S301 to step S304 in the extraction process illustrated in FIG. 11 are the same as those of step S201 to step S204 illustrated in FIG. 5, description thereof will be omitted. Furthermore, since processes of step S307 to step S310 in the extraction process illustrated in FIG. 11 are the same as those of step S207 to step S210 illustrated in FIG. 5, description thereof will be omitted.

In step S305 of FIG. 11, the extraction function 446 reads history information corresponding to the protocol of the executed scan. For example, when "whole body scan" is performed by the system control function 441, the extraction function 446 reads the history H11 to the history H14 illustrated in FIG. 3A from the memory 41 as history information starting from the "whole body scan".

Then, in step S306, the extraction function 446 extracts a candidate protocol on the basis of the history information and a result of the scan. For example, the extraction function 446 extracts, as a candidate protocol, a protocol executed according to the result of the executed scan among a plurality of protocols included in a plurality of history information read from the memory 41.

As an example, a case where the scan result "damage to the abdomen" is obtained in the "whole body scan" of the case A "examination at the time of traffic accident" will be described. In such a case, the extraction function 446 reads the history H11 to the history H14 illustrated in FIG. 3A from the memory 41 as history information starting from the "whole body scan". Then, the extraction function 446 extracts the "protocol P11" executed according to the scan result "damage to the abdomen" from among the three protocols "protocol P11", "protocol P14", and "protocol P16" that can be executed next to the "whole body scan" in the history H11 to the history H14. Then, the extraction function 446 outputs the identification information of the "protocol P11" to the output control function 447 as a candidate protocol.

In this way, the X-ray CT apparatus 1 according to the third embodiment can perform an extraction process by using history information.

Other Embodiments

Workflow without Branching

For example, in the aforementioned embodiment, the case where the workflow includes a branch has been described; however, the workflow does not necessarily include a branch. For example, the workflow may be protocol order information indicating the order of the protocols.

Figure 12:
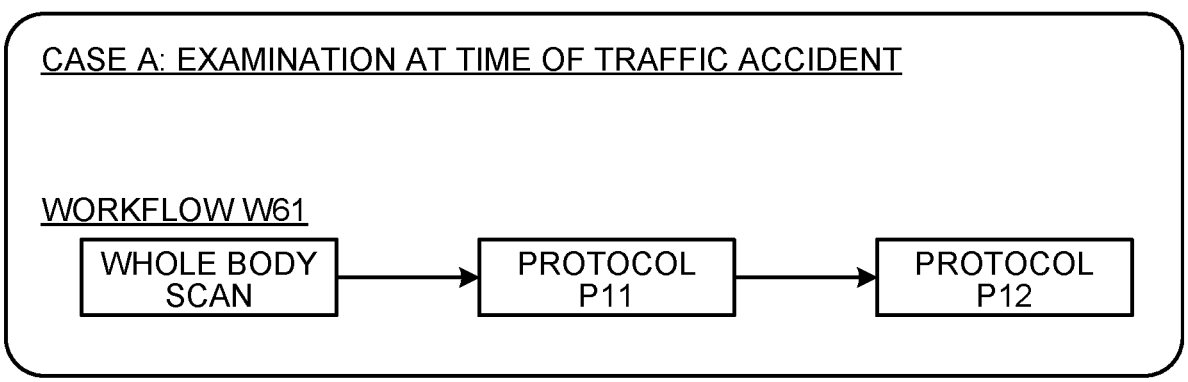
FIG. 12 is a diagram for explaining a workflow according to another embodiment.

FIG. 12 is a diagram for explaining a workflow according to another embodiment. FIG. 12 is an example of a workflow generated on the basis of the history H11 of FIG. 3A.

First, a generation process will be described. For example, a case where the history H11 of FIG. 3A exists and the history H12, the history H13, and the history H14 of FIG. 3A do not exist as the history information related to the case A "examination at the time of traffic accident" will be described. In such a case, the generation function 445 generates a workflow W61 illustrated in FIG. 12 on the basis of the history H11.

Specifically, the generation function 445 refers to the history H11, specifies the identification information of the "protocol P11" as a protocol executed next to the "whole body scan", and specifies the identification information of the "protocol P12" as a protocol executed next to the "protocol P11". Then, the generation function 445 generates the workflow W61 by correlating the identification information of each protocol with order information in which the protocols are executed. Since the workflow W61 includes no branch, the workflow W61 may not include a selection condition for selecting each protocol.

Next, an extraction process will be described. The extraction function 446 extracts a candidate protocol to be executed next to a protocol designated by a user, on the basis of protocol order information in which the identification information of each candidate protocol and the order information in which the candidate protocols are executed, are correlated with each other.

For example, when the workflow W61 of FIG. 12 exists and the "whole body scan" is designated by the user, the system control function 441 sends identification information of the designated "whole body scan" to the extraction function 446. Then, the extraction function 446 reads the workflow W61 starting from the designated "whole body scan" from the memory 41. Then, the extraction function 446 extracts a candidate protocol from the read workflow W61. Specifically, the extraction function 446 extracts the identification information of the "protocol P11" as a candidate protocol to be executed next to the "whole body scan". Furthermore, the extraction function 446 extracts the identification information of the "protocol P12" as a candidate protocol to be executed next to the "protocol P11". Then, the extraction function 446 outputs the identification information of the extracted candidate protocol to the output control function 447.

Then, the output control function 447 displays the candidate protocol. For example, the output control function 447 may individually (one by one) display the "protocol P11" and the "protocol P12", or display two (all) candidate protocols while indicating the order of the "protocol P11" and the "protocol P12", as protocols to be executed next.

In this way, the X-ray CT apparatus 1 can extract a candidate protocol to be executed next to a protocol designated by a user, on the basis of the protocol order information. In such a case, the extraction function 446 can extract a candidate protocol from the protocol order information without using a scan result (medical image analysis result).

Use of Patient Attribute Information

Furthermore, for example, the X-ray CT apparatus 1 can further use attribute information of a patient (subject). The attribute information is, for example, various information indicating the age, height, weight (degree of obesity), gender, and the like of the patient.

For example, the frequency of protocols used may vary depending on the age of a patient such as minors and the elderly. Furthermore, the frequency of protocols used may also vary depending on the height, weight, gender, and the like. Therefore, in the X-ray CT apparatus 1, the generation function 445 generates a workflow on the basis of the attribute information of the subject (generation process). Furthermore, the extraction function 446 extracts a candidate protocol on the basis of the attribute information of the subject (extraction process).

First, the generation process using the attribute information will be described. For example, the generation function 445 reads history information corresponding to specific attribute information such as the age, height, weight, and gender of a patient from the memory 41. Then, the generation function 445 generates a workflow on the basis of the history information corresponding to the specific attribute information.

As an example, among the histories H11 to H14 illustrated in FIG. 3A, when the history H11, the history H13, and the history H14 are history information of a minor and the history H12 is not the history information of the minor, the generation function 445 reads three pieces of history information of the history H11, the history H13, and the history H14 from the memory 41. Then, the generation function 445 generates a workflow of the minor on the basis of the history H11, the history H13, and the history H14. The generated workflow of the minor is stored in, for example, the memory 41. Note that the generation function 445 can generate a workflow on the basis of arbitrary attribute information, not limited to the "minor".

Next, the extraction process using the attribute information will be described. For example, the extraction function 446 reads the workflow corresponding to the specific attribute information such as the age, height, weight, and gender of the patient from the memory 41. Then, the extraction function 446 extracts a candidate protocol on the basis of the workflow corresponding to the specific attribute information.

As an example, a case where the subject is the minor will be described. In such a case, the extraction function 446 reads the workflow of the minor from the memory 41. Then, the extraction function 446 extracts a candidate protocol on the basis of the workflow of the minor.

Note that the aforementioned process is merely an example and the embodiment is not limited thereto. For example, the age may be correlated with each candidate protocol of the workflow and a candidate protocol corresponding to the age may be recommended in a preferential manner. Furthermore, the degree of obesity (weight and the like) may be correlated with each candidate protocol of the workflow and a candidate protocol may be recommended in a preferential manner according to the degree of obesity.

Omission (Skip) of Candidate Protocol Corresponding to Specific Attribute Information Furthermore, a specific candidate protocol can also be omitted (skipped) using the attribute information. That is, the extraction function 446 omits a candidate protocol corresponding to the attribute information of the subject.

For example, when the degree of obesity is above a certain level, the "Ca Score" is expected to be above a certain value. Therefore, in the recommended workflow R21 of FIG. 6C, when the degree of obesity of the subject is above a certain level, the extraction function 446 omits a scan for measuring the "Ca Score" and extracts the "protocol P22". With this, when the degree of obesity of the subject is above a certain level, the scan of the "Ca Score" is omitted and the scan of the "protocol P22" is recommended to a user.

Edition of Workflow

Furthermore, for example, when a plurality of processes included in each candidate protocol of a workflow are referred to and a common process exists, the workflow may be edited by moving the common process (overlapping process) to a candidate protocol in a previous stage or a subsequent stage, or deleting the common process (overlapping process).

First, the "movement of the common process" will be described. For example, the generation function 445 edits a workflow by moving a common process among a plurality of processes included in parallel candidate protocols to a candidate protocol in a previous stage or a subsequent stage of the candidate protocols. Note that the "processes" included in the candidate protocols correspond to, for example, a preparation scan, a reconstruction process, and the like.

Figure 13A:
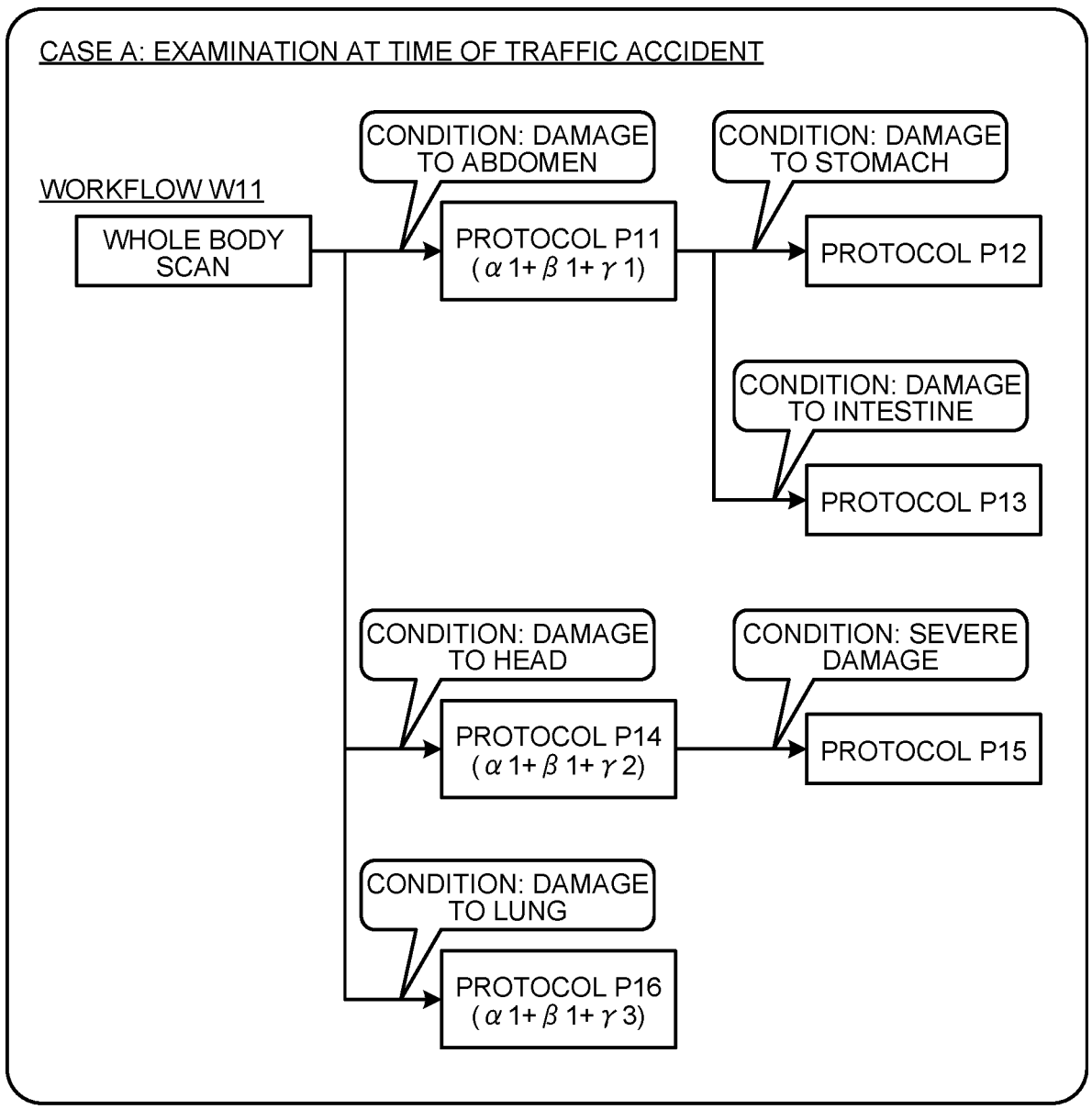
FIG. 13A to FIG. 13C are diagrams for explaining an editing process of a generation function according to another embodiment.
Figure 13B:
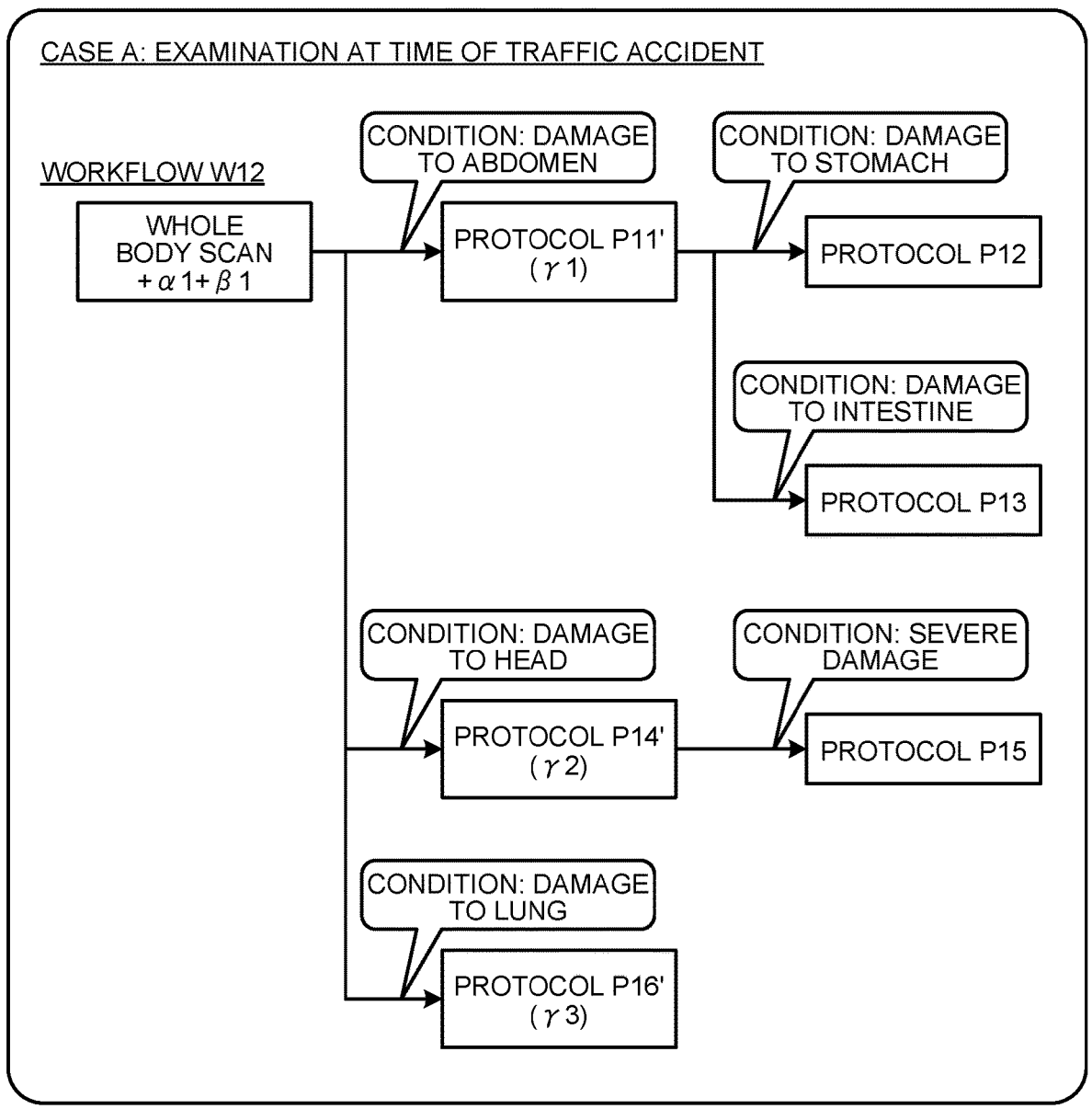
Figure 13C:
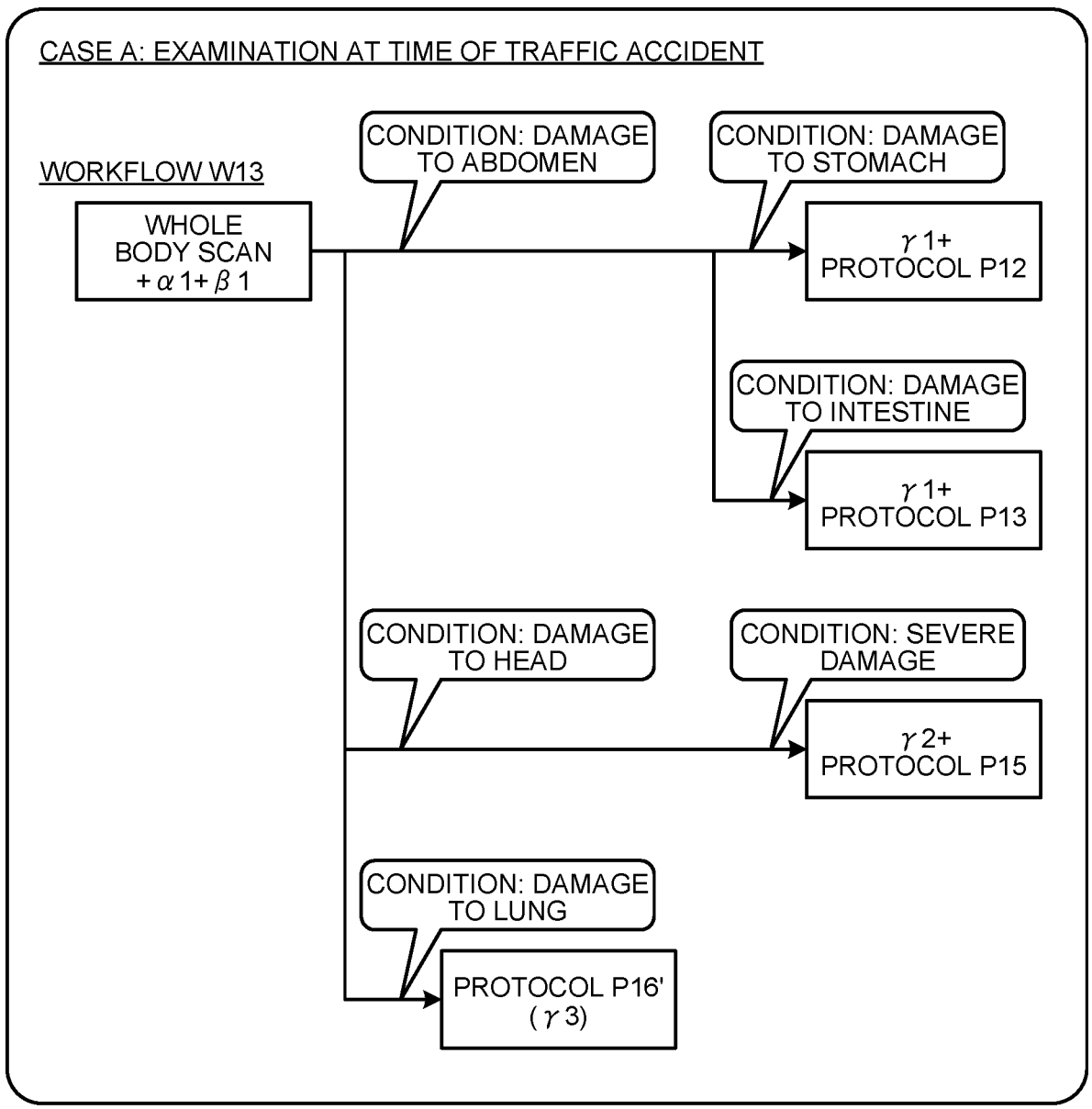

FIG. 13A, FIG. 13B, and FIG. 13C are diagrams for explaining the editing process of the generation function 445 according to another embodiment. FIG. 13A, FIG. 13B, and FIG. 13C illustrate a process when the workflow W11 of FIG. 4A is edited.

As illustrated in FIG. 13A, the workflow W11 may include a common process among the "protocol P11", the "protocol P14", and the "protocol P16" that are parallel candidate protocols. In the example of FIG. 13A, the "protocol P11" includes a process $\alpha1$, a process $\beta1$, and a process $\gamma1$. Furthermore, the "protocol P14" includes the process $\alpha1$, the process $\beta1$, and a process $\gamma2$. Furthermore, the "protocol P16" includes the process $\alpha1$, the process $\beta1$, and a process $\gamma3$. In such a case, the process $\alpha1$ and the process $\beta1$ are processes common to the "protocol P11", the "protocol P14", and the "protocol P16".

Therefore, as illustrated in FIG. 13B, the generation function 445 moves the process $\alpha1$ and the process $\beta1$, which are common processes in FIG. 13A, to the candidate protocol "whole body scan" in the previous stage, and changes the "whole body scan" to a "whole body scan+$\alpha1$+$\beta1$". The "whole body scan+$\alpha1$+$\beta1$" indicates that the whole body scan, the process $\alpha1$, and the process $\beta1$ are executed in order. As a consequence, the "protocol P11" is changed to a "protocol P11'" including the process $\gamma1$. Furthermore, the "protocol P14" is changed to a "protocol P14'" including the process $\gamma2$. Furthermore, the "protocol P16" is changed to a "protocol P16'" including the process $\gamma3$. With this, the workflow W11 is edited to a simpler workflow W12.

Moreover, as illustrated in FIG. 13C, the generation function 445 may also move the process $\gamma1$ and the process $\gamma2$ in FIG. 13B to the protocols in the subsequent stages, respectively. For example, the generation function 445 moves the process $\gamma1$ to the candidate protocols of "protocol P12" and "protocol P13" in the subsequent stage, thereby changing the "protocol P12" and the "protocol P13" to a "$\gamma1$+protocol P12" and a "$\gamma1$+protocol P13", respectively. The "$\gamma1$+protocol P12" indicates that the process $\gamma1$ and the protocol P12 are executed in order, and the "$\gamma1$+protocol P13" indicates that the process $\gamma1$ and the protocol P13 are executed in order. As a consequence, the "protocol P11'" and the "protocol P14'" in FIG. 13B are deleted. With this, the workflow W12 is edited to a simpler workflow W13.

Next, the "deletion of the common process" will be described. For example, the generation function 445 edits a workflow by deleting a common process among a plurality of processes included in candidate protocols arranged before and after.

Figure 14A:
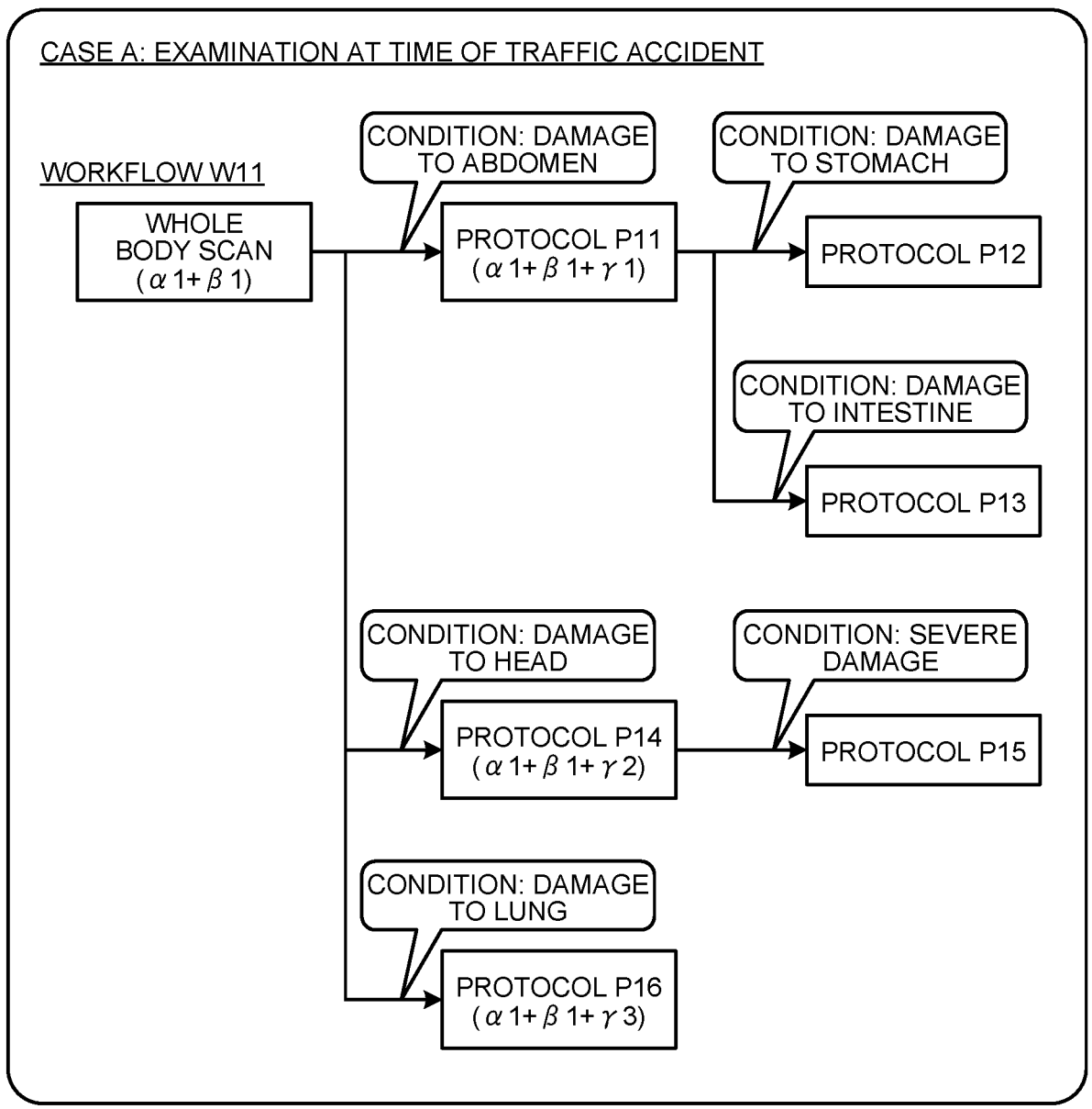
FIG. 14A and FIG. 14B are diagrams for explaining an editing process of a generation function according to another embodiment.
Figure 14B:
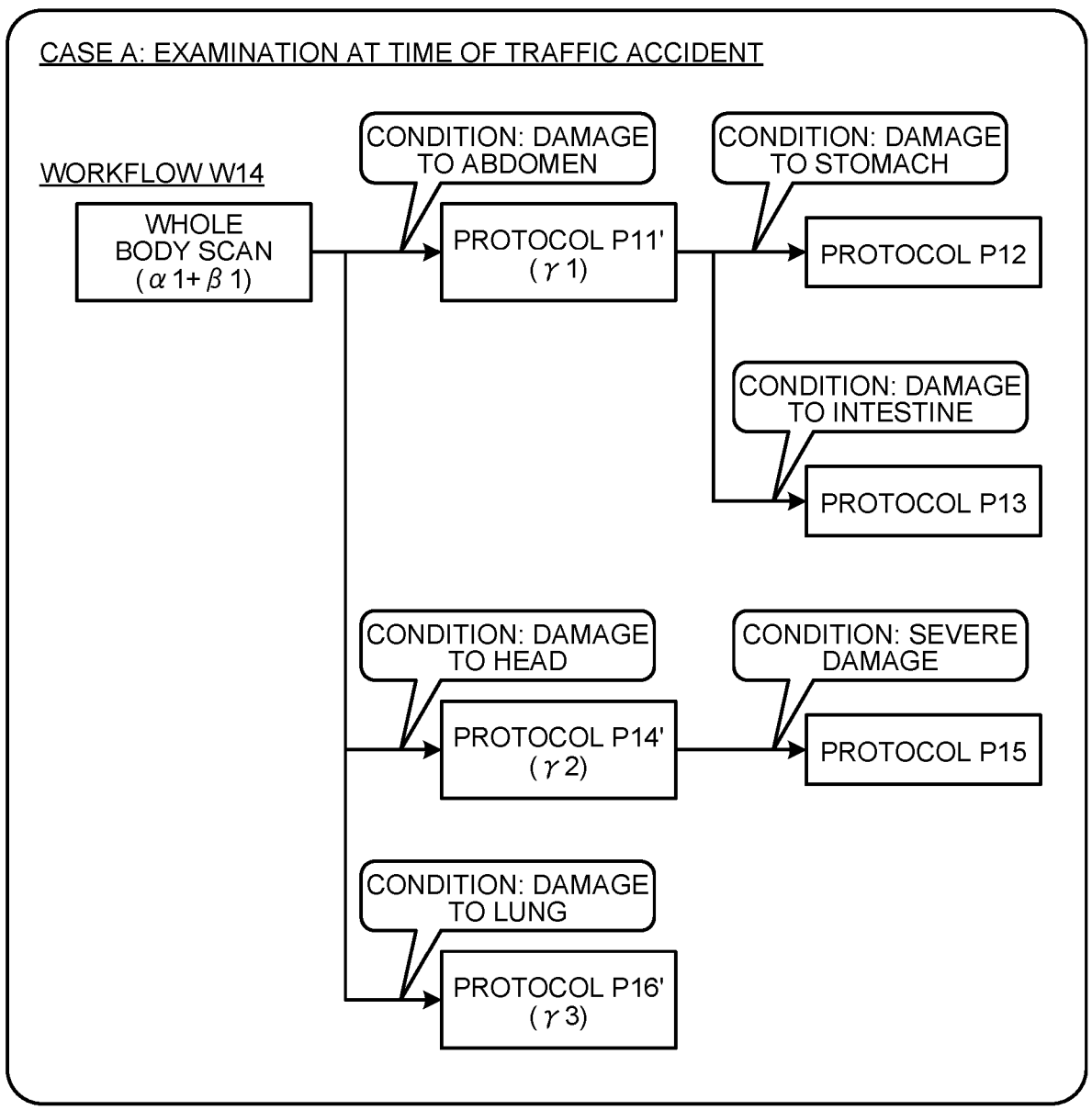

FIG. 14A and FIG. 14B are diagrams for explaining an editing process of the generation function 445 according to another embodiment. FIG. 14A and FIG. 14B illustrate a process when the workflow W11 of FIG. 4A is edited.

As illustrated in FIG. 14A, the workflow W11 may include a common process among the candidate protocol "whole body scan" in the previous stage and the candidate protocols "protocol P11", "protocol P14", and "protocol P16" in the subsequent stage. In the example of FIG. 14A, the "whole body scan" includes the process $\alpha1$ and the process $\beta1$. Furthermore, the "protocol P11" includes the process $\alpha1$, the process $\beta1$, and the process $\gamma1$. Furthermore, the "protocol P14" includes process $\alpha1$, process $\beta1$, and process $\gamma2$. Furthermore, the "protocol P16" includes process $\alpha1$, process $\beta1$, and process $\gamma3$. In such a case, the process $\alpha1$ and the process $\beta1$ are processes common to the "whole body scan", the "protocol P11", the "protocol P14", and the "protocol P16".

Therefore, as illustrated in FIG. 14B, the generation function 445 deletes the process $\alpha1$ and the process $\beta1$, which are common processes in FIG. 14A, from the candidate protocols "protocol P11", "protocol P14", and "protocol P16" in the subsequent stages, respectively. As a consequence, the "protocol P11" is changed to a "protocol P11'" including the process $\gamma1$. Furthermore, the "protocol P14" is changed to a "protocol P14'" including the process $\gamma2$. Furthermore, the "protocol P16" is changed to a "protocol P16'" including the process $\gamma3$. With this, the workflow W11 is edited to a simpler workflow W14.

Although not illustrated in the drawings, the generation function 445 may also move the process $\gamma1$ and the process $\gamma2$ in FIG. 14B to the protocols in the subsequent stages, respectively. For example, the generation function 445 moves the process $\gamma1$ to the candidate protocols "protocol P12" and "protocol P13" in the subsequent stages, thereby changing the "protocol P12" and the "protocol P13" to a "$\gamma1$+protocol P12" and a "$\gamma1$+protocol P13", respectively. As a consequence, the "protocol P11'" and the "protocol P14'" can be deleted as in FIG. 13C.

Note that the contents described in FIG. 13A to FIG. 13C and FIG. 14A and FIG. 14B are merely examples and the embodiment is not limited thereto. For example, even when a common process exists among the "protocol P11", the "protocol P12", and the "protocol P13", or even when a common process exists between the "protocol P14" and the "protocol P15", the common process can be moved or deleted in the same manner.

In this way, the generation function 445 can reduce the number of processes included in a workflow and simplify the workflow by specifying a process common to protocols and moving or deleting the common process. As a consequence, the X-ray CT apparatus 1 can provide a simpler and easy-to-use workflow for engineers or doctors who actually take the lead in an examination.

Medical Information Processing System

Furthermore, for example, the processes according to the aforementioned embodiment can be provided as a server device (image processing server) on a network. The server device can provide, for example, an information processing service (cloud service) via the network.

For example, the server device performs an interpretation alert function. That is, the server device receives a medial image imaged by a medical image diagnostic apparatus such as an X-ray CT apparatus and performs an analysis process before interpretation. Then, the server device analyzes whether an urgent abnormality exists in the analysis process, and issues an alert in an interpretation request list (list of images waiting for interpretation) to increase the priority of interpretation when the abnormality is found. Similarly to the aforementioned "analysis application", the "analysis process" detects a feature in an image as an "abnormality" by image analysis, or detects an "abnormality" by comparing an arbitrary parameter obtained from an image with a threshold value. That is, the interpretation alert function can generate information corresponding to the "scan result" described in the first embodiment, such as information on a damage site and the value of an Agatston score, by the analysis process.

The server device according to the present embodiment can perform at least one of the "generation process" of the workflow and the "extraction process" of the candidate protocol according to the aforementioned embodiment, in addition to the interpretation alert function.

Figure 15:
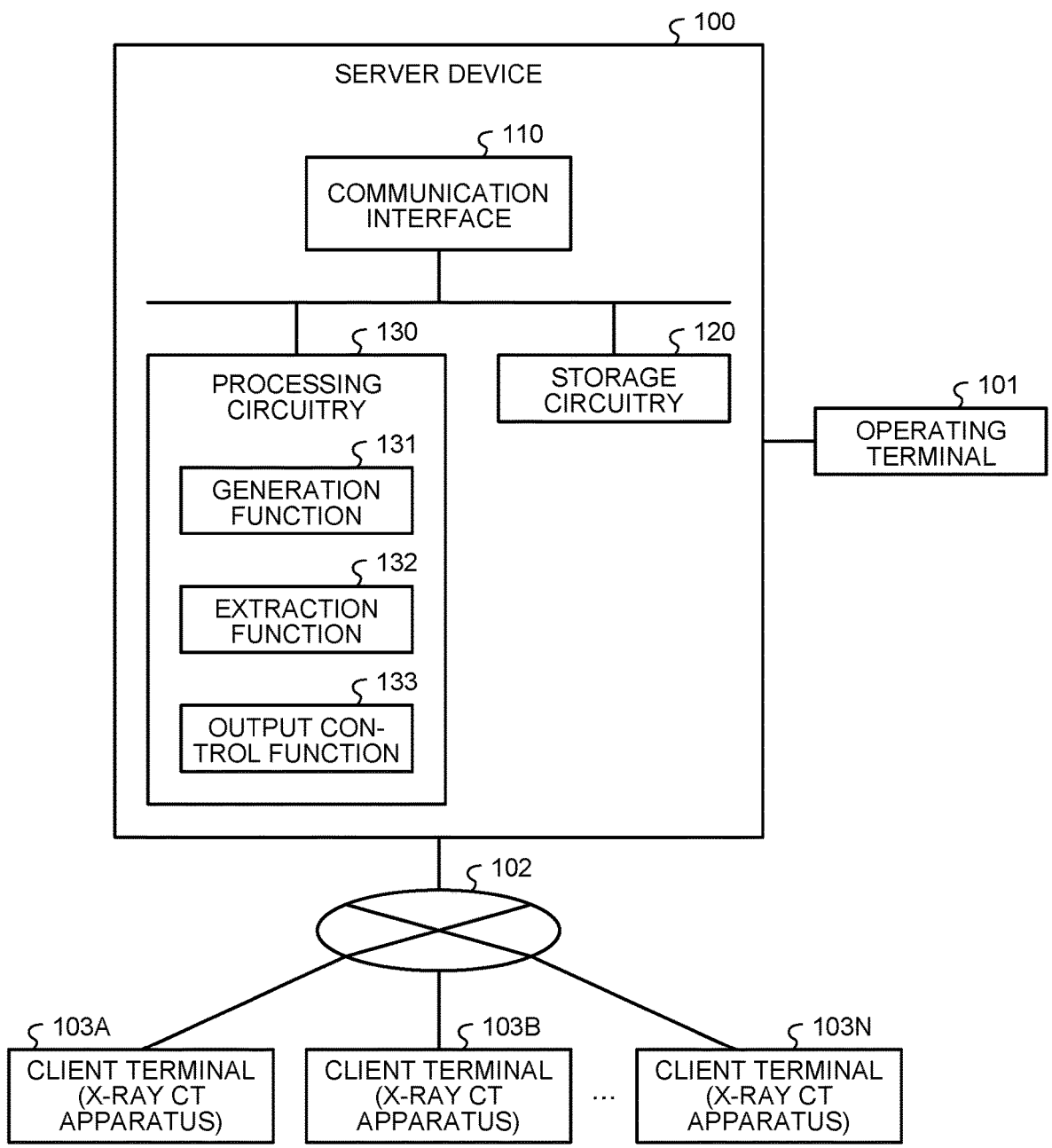
FIG. 15 is a block diagram illustrating an example of a configuration of a medical information processing system according to another embodiment.

FIG. 15 is a block diagram illustrating an example of a configuration of a medical information processing system according to another embodiment. As illustrated in FIG. 15, for example, a server device 100 is installed in a service center that provides an information processing service. The server device 100 is connected to an operating terminal 101. Furthermore, the server device 100 is connected to a plurality of client terminals 103A, 103B, . . . , 103N via a network 102. Note that the server device 100 and the operating terminal 101 may also be connected via the network 102. Furthermore, when the client terminals 103A, 103B, . . . , 103N are generally referred without distinction, they are described as a "client terminal 103". Furthermore, the medical information processing system includes the server device 100 and the client terminal 103.

The operating terminal 101 is an information processing terminal used by a person (operator) who operates the server device 100. For example, the operating terminal 101 includes an input device such as a mouse, a keyboard, and a touch panel for receiving various instructions and setting requests from the operator. Furthermore, the operating terminal 101 includes a display device for displaying an image or displaying a GUI used when the operator inputs various setting requests by using the input device. The operator can transmit various instructions and setting requests to the server device 100 or browse information inside the server device 100 by operating the operating terminal 101. Furthermore, the network 102 is an arbitrary communication network such as the Internet, a wide area network (WAN), and a local area network (LAN).

The client terminal 103 is an information processing terminal operated by a user who uses an information processing service. The user is, for example, a medical worker such as a doctor and an engineer who work in a medical institution. For example, the client terminal 103 corresponds to an operating terminal of a medical image diagnostic apparatus such as a console device included in an X-ray CT apparatus. The client terminal 103 has a client function enabling use of the information processing service provided by the server device 100. Note that the client function is pre-recorded in the client terminal 103 in the form of a computer program that can be executed by a computer. Furthermore, the client terminal 103 may be an information processing device such as a personal computer and a workstation connected to the medical image diagnostic apparatus.

The server device 100 includes a communication interface 110, storage circuitry 120, and processing circuitry 130. The communication interface 110, the storage circuitry 120, and the processing circuitry 130 are communicably connected to one another.

The communication interface 110 is, for example, a network card or a network adapter. The communication interface 110 is connected to the network 102 to perform information communication between the server device 100 and an external device.

The storage circuitry 120 is, for example, a Not AND (NAND)-type flash memory or a hard disk drive (HDD), and stores therein various computer programs for displaying medical image data and GUI, and information to be used by the computer programs.

The processing circuitry 130 is an electronic device (processor) that controls the overall processing in the server device 100. The processing circuitry 130 performs a generation function 131, an extraction function 132, and an output control function 133. The processing functions performed by the processing circuitry 130 are recorded in the storage circuitry 120 in the form of computer programs that can be executed by a computer, for example. The processing circuitry 130 reads and executes the computer programs, thereby implementing the functions corresponding to the respective read computer programs. The generation function 131, the extraction function 132, and the output control function 133 can perform basically the same processing as the generation function 445, the extraction function 446, and the output control function 447 illustrated in FIG. 1.

First, the "generation process" in the server device 100 will be described. For example, the storage circuitry 120 of the server device 100 stores therein history information. The history information is collected from the client terminals 103. The timing at which the history information is collected is as follows, for example: the history information may be collected each time a scan is executed by each protocol, and may be collectively collected at the timing when the generation process is performed by the server device 100.

Then, the generation function 131 performs the generation process of generating a workflow on the basis of the collected history information. Since the generation process is the same as the process illustrated in FIG. 2, for example, description thereof will be omitted. Then, the output control function 133 stores the generated workflow in the storage circuitry 120 or a storage device (memory 41 or the like) of each client terminal 103. For example, preferably, the workflow is stored in the storage circuitry 120 when the extraction process is performed by the server device 100, and is stored in the storage device of each client terminal 103 when the extraction process is performed by each client terminal 103.

Next, the "extraction process" in the server device 100 will be described. For example, each time a scan is executed, each client terminal 103 transmits (uploads) a medical image obtained by the scan to the server device 100. Note that the transmission of the medical image may be automatically performed by each client terminal 103, or may be manually performed (manually operated) by a user.

Then, the extraction function 132 performs the extraction process of extracting a candidate protocol on the basis of the workflow. The extraction process is basically the same as illustrated in FIG. 5, for example, but by acquiring the processing result of the analysis process performed by the aforementioned interpretation alert function, a common process (overlapping process) can be omitted. That is, when the information corresponding to the scan result has been generated by the interpretation alert function of the server device 100, the extraction function 132 acquires the information corresponding to the scan result from the interpretation alert function. With this, the extraction function 132 can omit a process corresponding to step S204 of FIG. 5.

Then, the output control function 133 transmits (downloads) the extracted candidate protocol to each client terminal 103. Specifically, the output control function 133 transmits the candidate protocol to the client terminal 103 that is a transmission source of the medical image.

In this way, the server device 100 can perform the workflow generation process and the candidate protocol extraction process in addition to the interpretation alert function. With this, a user of each client terminal 103 can easily select an appropriate protocol.

Note that the aforementioned process is merely examples and the embodiment is not limited thereto. For example, an arbitrary function of the interpretation alert function, the generation process, and the extraction process may be performed by the client terminal 103 or another external device. For example, the interpretation alert function and the generation process may be performed by the server device 100, and the extraction process may be performed by the client terminal 103 (such as the console device of X-ray CT apparatus).

In addition to the aforementioned embodiments, various different embodiments may also be implemented.

Medical Image Diagnosis Apparatus

In the above embodiments, the cases where the processing according to the above embodiments is executed by the X-ray CT apparatus 1 have been described; however, embodiments are not limited thereto. The processing according to the above embodiments can also be performed by, for example, other medical image diagnosis apparatuses, such as magnetic resonance imaging (MRI) apparatuses and ultrasonic diagnostic apparatuses, as well as the X-ray CT apparatus 1.

Furthermore, the respective components of the respective apparatuses illustrated in the drawings are functional conceptual ones and do not necessarily have to be physically configured as illustrated in the drawings. That is, specific forms of distribution and integration of the respective apparatuses are not limited to those illustrated in the drawings and all or some of the apparatuses can be configured to be distributed or integrated functionally or physically in any units depending on various loads, usage conditions, and the like. Moreover, all or any part of processing functions performed by the respective apparatuses can be implemented by a CPU and a computer program analyzed and executed by the CPU, or can be implemented as hardware by wired logic.

Furthermore, among the respective processes described in the aforementioned embodiments and modifications, all or some of the processes described as being automatically performed can also be manually performed, or all or some of the processes described as being manually performed can also be automatically performed by a known method. In addition, processing procedures, control procedures, specific names, and information including various data and parameters indicated in the aforementioned specification and the drawings can be modified in any manner unless otherwise specified.

Furthermore, the scanning method described in the aforementioned embodiments and modifications can be implemented by executing a scanning program prepared in advance on a computer such as a personal computer and a work station. The scanning program can be distributed via a network such as the Internet. Furthermore, the scanning program can also be executed by being recorded on a non-transitory recording medium such as a hard disk, a flexible disk (FD), a CD-ROM, a MO, and a DVD that can be read by a computer, and being read from the recording medium by the computer.

According to at least one embodiment described above, it is possible to easily select an appropriate protocol.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising processing circuitry configured:
   to execute a scan based on a protocol designated by a user,
   to generate branch information indicating branches from a specific protocol to a next protocol by correlating identification information that indicates each of a plurality of candidate protocols that is executable starting from the specific protocol, order information in which each candidate protocol is executed, and a selection condition for selecting each candidate protocol with each other,
   to extract a candidate protocol to be executed next to the designated protocol, based on the branch information, and
   to output the extracted candidate protocol.

2. The medical image diagnostic apparatus according to claim 1, wherein
   the processing circuitry extracts the candidate protocol to be executed next to the designated protocol, based on the branch information and a result of the scan.

3. The medical image diagnostic apparatus according to claim 2, further comprising:
   storage circuitry configured to store therein history information including both information indicating a protocol executed next to the specific protocol and a result of a scan by each protocol, wherein
   the processing circuitry further generates the branch information based on the history information.

4. The medical image diagnostic apparatus according to claim 3, wherein the processing circuitry edits the branch information by moving a common process among a plurality of processes included in parallel candidate protocols to the candidate protocol in a previous stage or a subsequent stage of the candidate protocols.

5. The medical image diagnostic apparatus according to claim 3, wherein the processing circuitry edits the branch information by deleting a common process among a plurality of processes included in candidate protocols arranged before and after.

6. The medical image diagnostic apparatus according to claim 3, wherein the processing circuitry further generates the branch information based on attribute information of a subject.

7. The medical image diagnostic apparatus according to claim 2, wherein the processing circuitry further extracts the candidate protocol based on attribute information of a subject.

8. The medical image diagnostic apparatus according to claim 7, wherein the processing circuitry further omits the candidate protocol corresponding to the attribute information of the subject.

9. The medical image diagnostic apparatus according to claim 2, wherein the processing circuitry acquires the result of the scan by inputting a medical image obtained by the scan into an analysis application.

10. The medical image diagnostic apparatus according to claim 2, wherein the processing circuitry extracts identification information of the candidate protocol corresponding to the selection condition according to the result of the scan from among a plurality of candidate protocols included in the branch information.

11. The medical image diagnostic apparatus according to claim 2, wherein the processing circuitry extracts a parameter to be changed based on the branch information and the result of the scan, and outputs the parameter to be changed.

12. The medical image diagnostic apparatus according to claim 2, wherein the processing circuitry transmits the branch information to an external device.

13. The medical image diagnostic apparatus according to claim 2, wherein the processing circuitry receives branch information generated by an external device and stores the received branch information in a storage unit.

14. The medical image diagnostic apparatus according to claim 2, wherein the processing circuitry further changes the branch information based on an instruction from a user.

15. The medical image diagnostic apparatus according to claim 14, wherein the processing circuitry changes the branch information based on history information including both information indicating a protocol executed next to the specific protocol and a result of a scan by each protocol, and the branch information.

16. The medical image diagnostic apparatus according to claim 15, wherein the processing circuitry generates a change plan of the branch information based on the history information including both information indicating a protocol executed next to the specific protocol and a result of a scan by each protocol, and the branch information, and changes the branch information based on the change plan when the change plan is approved by a user.

17. The medical image diagnostic apparatus according to claim 15, wherein the processing circuitry receives branch information transmitted from an external device, stores the received branch information in a storage unit, and changes the branch information generated by the external device based on history information stored in the medical image diagnostic apparatus.

18. The medical image diagnostic apparatus according to claim 2, wherein the processing circuitry extracts the candidate protocol to be executed next, based on history information including both identification information indicating a protocol executed next to the specific protocol and a result of a scan by each protocol.

19. A computer program product having a non-transitory computer readable medium including a plurality of programmed instructions, wherein the instructions, when executed by a computer, cause the computer to perform:
    executing a scan based on a protocol designated by a user;
    generating branch information indicating branches from a specific protocol to a next protocol by correlating identification information that indicates each of a plurality of candidate protocols that is executable starting from the specific protocol, order information in which each candidate protocol is executed, and a selection condition for selecting each candidate protocol with each other;
    extracting a candidate protocol to be executed next to the designated protocol, based on the branch information; and
    outputting the extracted candidate protocol.

20. A medical information processing system comprising processing circuitry configured:
    to execute a scan based on a protocol designated by a user,
    to generate branch information indicating branches from the specific protocol to a next protocol by correlating identification information that indicates each of a plurality of candidate protocols that is executable starting from a specific protocol, order information in which each candidate protocol is executed, and a selection condition for selecting each candidate protocol with each other,
    to extract a candidate protocol to be executed next to the designated protocol, based on the branch information, and
    to output the extracted candidate protocol.

21. A medical image diagnostic apparatus comprising processing circuitry configured:
    to execute a scan based on a protocol selected by a user,
    to generate branch information in which identification information indicating a next protocol executed next to a specific protocol and a selection condition for selecting each next protocol are correlated with each other, based on history information including the identification information and a result of a scan by each protocol,
    to extract a candidate protocol to be executed next to the selected protocol, based on the branch information and the result of the scan, and
    to output the extracted candidate protocol.

22. A computer program product having a non-transitory computer readable medium including a plurality of programmed instructions, wherein the instructions, when executed by a computer, cause the computer to perform:
    executing a scan based on a protocol selected by a user;
    generating branch information in which identification information indicating a protocol executed next to a specific protocol and a selection condition for selecting each next protocol are correlated with each other, based on history information including the identification information and a result of a scan by each protocol, and
    extracting a candidate protocol to be executed next to the selected protocol, based on the branch information and the result of the scan, and
    outputting the extracted candidate protocol.

* * * * *